United States Patent
Choi et al.

(10) Patent No.: US 10,415,068 B2
(45) Date of Patent: *Sep. 17, 2019

(54) MICROORGANISM FOR PRODUCTION OF PUTRESCINE AND METHODS FOR PRODUCTION OF PUTRESCINE USING THE SAME

(71) Applicants: CJ CHEILJEDANG CORPORATION, Seoul (KR); KOREA ADVANCED INSTITUTE OF SCIENCE AND TECHNOLOGY, Daejeon (KR)

(72) Inventors: Hyang Choi, Gyeonggi-do (KR); Hee Kyoung Jung, Seoul (KR); Hak Sung Kim, Daejeon (KR); Hyun Ho Kyeong, Daejeon (KR); Jung Min Choi, Daejeon (KR); Joong Jae Lee, Daejeon (KR); Hyo Deok Seo, Daejeon (KR)

(73) Assignees: Korea Advanced Institute of Science and Technology, Daejeon (KR); CJ Cheiljedang Corporation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/179,134

(22) Filed: Nov. 2, 2018

(65) Prior Publication Data

US 2019/0055587 A1 Feb. 21, 2019

Related U.S. Application Data

(62) Division of application No. 14/905,793, filed as application No. PCT/KR2014/006490 on Jul. 17, 2014, now Pat. No. 10,160,981.

(30) Foreign Application Priority Data

Jul. 17, 2013 (KR) .................. 10-2013-0084409

(51) Int. Cl.
C12P 13/00 (2006.01)
C12N 9/88 (2006.01)

(52) U.S. Cl.
CPC .............. *C12P 13/001* (2013.01); *C12N 9/88* (2013.01); *C12Y 401/01017* (2013.01)

(58) Field of Classification Search
CPC .. C12P 13/001; C12N 9/88; C12Y 401/01017
See application file for complete search history.

(56) References Cited

U.S. PATENT DOCUMENTS 3,668,072 A 6/1972 Ando et al.

FOREIGN PATENT DOCUMENTS

| KR | 10-2012-0064045 A | 6/2012 |
|---|---|---|
| KR | 10-2012-0064046 A1 | 6/2012 |
| WO | WO 2006/005603 A1 | 1/2006 |
| WO | WO 2012/077995 A2 | 6/2012 |
| WO | WO 2013/105827 A2 | 7/2013 |

OTHER PUBLICATIONS

Appplebaum et al., "Comparison of the Biosynthetic and Biodegradative Omithine Decarboxylases of *Escherichia coli*," Biochemistry 16(8): 1580-1584, 1977.
Momany et al., "Structural motifs for pyridoxal-5'-phosphate binding in decarboxylases: An analysis based on the rystal structure of the Lactobacillus 30a ornithine decarboxylase CORY," Protein Science 4: 849-854, 1995.
Osterman et al., "Acidic Residues Important for Substrate Binding and Cofactor Reactivity in Eukaryotic Ornithine Decarboxylase Identified by Alanine Scanning Mutagenesis," The Journal of Biological Chemistry 270(20):11797-11802, May 19, 1995.
Qian et al., "Metabolic Engineering of *Escherichia coli* for the Production of Putrescine: A Four Carbon Diamine," Biotechnol. Bioeng. 104: 651-662, 2009.
Schneider et al., "Putrescine production by engineered Corynebacterium glutamicum," Appl. Microbiol. Biotechnol. 88:859-868, 2010.
Choi et al., "Rational design of omithine decarboxylase with catalytic activity for the production of putrescine," Appl. Microbiol. Biotechnol. 98: 7483-7490, 2014.
Stover et al., PIR accession No. D83418, Sep. 15, 2000, 2 pages.
Branden et al., Introduction to Protein Structure, Garland Publishing Inc., New York, p. 247.
Witkowski et al., "Conversion of a beta-ketoacyl synthase to a malonyl decarboxylase by replacement of the active-site cysteine with glutamine," Biochemistry 38:11643-11650, 1999.
Seffernick et al., "Melamine deaminase and atrazine chlorohydrolase: 98 percent identical but functionally different," J. Bacteriol. 183(8):2405-2410, 2001.
Sadowski et al., "The sequence-structure relationship and protein function prediction," Current Opinion in Structural Biology 19(3):357-362, 2009.
UniProtkB-P21169(DCOR_ECOLI), uniprot database, retrieved online Jun. 20, 2018 from https://www.uniprot.org/uniprot/P21169 Jun. 20, 2018, 5 pages.
Chen Yong et al., "Rational design of Novel Enzymes," Pharmaceutical Biotechnology, vol. 18, issue 8, pp. 538-543 (2011).
GenBank ID AAA66174.1, ornithine decarboxylase (speC) (EC 4.1.1.17) [*Escherichia coli*], dated May 11, 1995, 1 page.

*Primary Examiner* — Delia M Ramirez
(74) *Attorney, Agent, or Firm* — Cooley LLP

(57) ABSTRACT

Provided are a novel modified ornithine decarboxylase protein having improved putrescine productivity and a use thereof.

14 Claims, 1 Drawing Sheet
Specification includes a Sequence Listing.

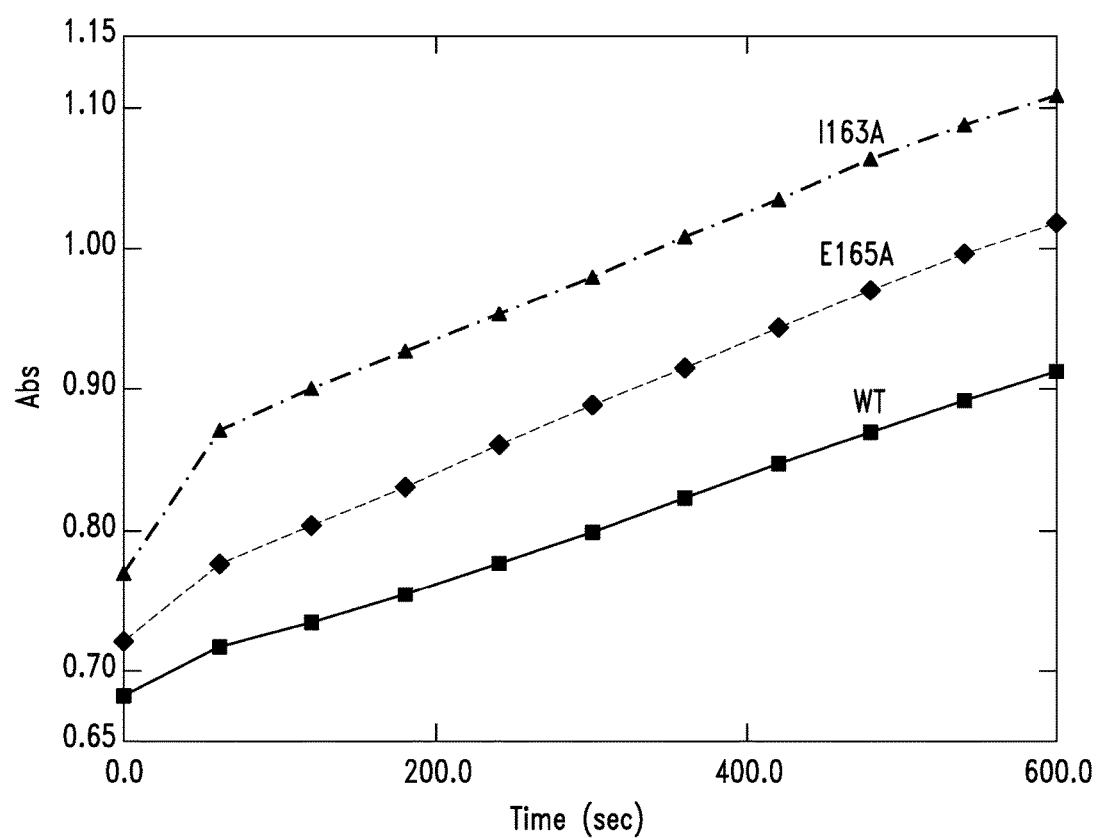

US 10,415,068 B2

MICROORGANISM FOR PRODUCTION OF PUTRESCINE AND METHODS FOR PRODUCTION OF PUTRESCINE USING THE SAME

CROSS-REFERENCE TO RELATED APPLICATIONS

This application is a divisional of U.S. application Ser. No. 14/905,793, filed Jan. 16, 2016, now U.S. Pat. No. 10,160,981, which is a U.S. national phase application of International PCT Patent Application No. PCT/KR2014/006490, which was filed Jul. 17, 2014, which claims priority to Korean Patent Application No. 10-2013-0084409, filed Jul. 17, 2013. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_042_01US_ST25.txt. The text file is 158 KB, was created on Nov. 2, 2018, and is being submitted electronically via EFS-Web.

TECHNICAL FIELD

The present disclosure relates to a novel modified ornithine decarboxylase protein and a use thereof.

BACKGROUND ART

Putrescine (or 1,4-butanediamine) is an important raw material for the production of polyamide-4,6 including nylon-4,6, and is mainly produced on an industrial scale by the hydrogenation of succinonitrile, which is produced from acrylonitrile by addition of hydrogen cyanide. The chemical synthesis of this compound requires non-renewable petrochemical products as raw materials, and relatively high temperature and pressure in a multi-step and multi-reactor design, as well as the use of expensive catalyst systems. Furthermore, since these raw materials are highly toxic and flammable, the known chemical synthetic processes are environmentally disadvantageous. Accordingly, as an alternative to the chemical production process, a process of producing putrescine from a renewable biomass-derived carbon source is required. Recently, a biochemical process of producing putrescine by environmentally friendly microorganisms has received much attention. Putrescine is a kind of polyamine which is found in a broad spectrum of organisms ranging from bacteria to animals and plants. The concentration of putrescine in *E. coli* is known to be extremely high, as much as about 2.8 g/L. Also, microorganisms have potentially good resistance to high concentrations of polyamines, and thus they are able to grow and survive in the presence of high concentrations thereof. For example, it has been reported that *Corynebacterium glutamicum* can grow even in the presence of more than 30 g/L of cadaverine. Accordingly, Studies have been continuously conducted to use microorganisms in the production of industrially available high-concentration polyamines. However, studies on the production of polyamines using microorganisms have not advanced enough to be industrially applicable. Therefore, it is aneed to develop a strain capable of producing polyamines in a high yield (Qian Z G, et al., Biotechnol Bioeng, 104: 651-662, 2009; Schneider J, et al., Appl Microbiol Biotechnol, 88: 859-868, 2010).

Meanwhile, ornithine decarboxylase (ODC) is an enzyme found in most microorganisms which converts ornithine into putrescine. ODC in *E. coli* generally forms a homodimer, and active sites are formed at the dimer interface. The reaction mechanism of ODC requires pyridoxal phosphate (PLP) as a cofactor, and PLP forms a Schiff base at a lysine residue of the active site of the enzyme, which is later displaced by a substrate ornithine that undergoes decarboxylation. When putrescine is produced, ODC again forms a Schiff base with PLP.

When ODC introduced into a putrescine-producing strain, genus *Corynebacterium*, is a protein encoded by *E. coli* speC gene, and its activity is reported to be very low. Therefore, in order to develop a strain producing putrescine in a high yield, improvement of ODC, which is an enzyme involved in the final step of the putrescine biosynthetic pathway, is very important. Until now, mutation researches have been performed only to the structure or reaction mechanism of an ODC protein, and there have been no reports regarding an increase activity thereof.

DISCLOSURE

Technical Problem

The present inventors have made many efforts to improve an ODC protein, which plays an important role in the production of putrescine but shows low activity. As a result, they have discovered a novel mutation site and introduced a mutation on the site to prepare a modified ODC protein having improved putrescine-producing activity, and they have found that when the modified ODC protein is introduced into a putrescine-producing microorganism, the microorganism is able to produce putrescine in a high yield, thereby completing the present application.

Technical Solution

An object of the present invention is to provide a novel modified ornithine decarboxylase (ODC) protein.

Another object of the present invention is to provide a polynucleotide encoding the modified ODC protein, a vector including the polynucleotide, and a transformant transformed with the vector.

Still another object of the present invention is to provide a method of preparing putrescine, the method including the step of reacting L-ornithine, a mixture containing L-ornithine, or an L-ornithine fermentation liquid with the modified ODC protein.

Still another object of the present invention is to provide a recombinant microorganism which has an improved putrescine-producing activity by changing to the modified ODC protein in a *Corynebacterium* sp. microorganism having putrescine-producing activity.

Still another object of the present invention is to provide a method of producing putrescine, the method including the steps of culturing the *Corynebacterium* sp. microorganism which has improved putrescine-producing activity by introduction of the modified ODC protein; and recovering putrescine from a culture obtained in the above step.

Advantageous Effects

A modified ornithine decarboxylase protein according to the present invention has putrescine conversion activity which is 21-fold higher than that of a native form. When the modified ornithine decarboxylase protein introduced into a putrescine-producing strain, putrescine productivity is remarkably increased. Therefore, it may be widely applied to efficient mass production of putrescine as an alternative to the known chemical synthetic pathway.

DESCRIPTION OF DRAWINGS

FIG. 1 shows a comparison of putrescine conversion activity between a native E. coli-derived ODC protein and the ODC protein having an I163A or E165A mutation. In detail, pH increases while a conversion reaction occurs, and when the pH increase is examined by phenol red, an increase in absorbance is observed. The ODC protein having I163A or E165A or both of the mutations was found to show superior putrescine conversion activity compared to the native ODC protein.

BEST MODE

In an aspect to achieve the above objects, the present invention provides a novel modified ODC protein, the modified ODC protein having mutation at one or more amino acid residues selected from the group consisting of an isoleucine amino acid residue at position 163 and a glutamic acid amino acid residue at position 165 from an N-terminus of ornithine decarboxylase (ODC) having an amino acid sequence represented by SEQ ID NO: 1.

As used herein, the term "ornithine decarboxylase (ODC)" refers to an enzyme that catalyzes the following reaction which is the first step of the synthesis of a polyamine from ornithine and the last step of the putrescine synthetic pathway. In the production of putrescine using L-ornithine as a substrate, pyridoxal phosphate (PLP) functions as a cofactor.

L-ornithine<=>putrescine+$CO_2$    [Reaction Scheme]

In the present invention, ornithine decarboxylase (ODC) may be specifically ODC derived from E. coli, and more specifically, ODC having an amino acid sequence represented by SEQ ID NO: 1, which is derived from Escherichia coli.

In the present invention, a method of obtaining ODC (ornithine decarboxylase) may be performed by applying a variety of methods known in the art. For example, ODC may be obtained by gene synthesis technology including codon optimization for obtaining the enzyme in a high yield in E. coli which is generally used in the enzyme expression, and a method of screening useful enzyme resources by bioinformatics based on genome information of the microorganism, but is not limited thereto.

As used herein, the term "modified ODC protein" refers to an ODC protein in which one or more amino acids in the amino acid sequence of the ODC protein are added, deleted, or substituted. Specifically, the modified ODC protein refers to a protein in which the activity thereof is efficiently increased by the modification of a ODC protein compared to that of the wild-type. In the present invention, the modification may be performed using any general method of improving enzymes which is known in the art, without limitation, and the method is exemplified by strategies such as rational design and directed evolution. For example, the rational design strategy may include mutation in an amino acid at a particular site (site-directed mutagenesis), and the directed evolution strategy may include random mutagenesis. Further, natural modification(s) may occur at amino acid residue(s) at position 163 and/or at position 165 of SEQ ID NO: 1 without external manipulation. As used herein, the terms "modified ODC protein", "ODC mutant", and "speC mutant" may be used interchangeably.

Specifically, the modified ODC protein of the present invention may have modification(s) of an isoleucine amino acid residue at position 163 and/or a glutamic acid amino acid residue at position 165 from the N-terminus of ornithine decarboxylase (ODC) which is derived from Escherichia coli and has an amino acid sequence represented by SEQ ID NO: 1. For example, the glutamic acid at position 165 may be replaced with alanine, glycine, serine, or valine, or the isoleucine at position 163 may be replaced with alanine, glycine, serine, or valine. Further, the modified ODC protein may have a double modification of the isoleucine at position 163 and the glutamic acid at position 165, in which the isoleucine at position 163 and the glutamic acid at position 165 may be replaced with an amino acid selected from the group consisting of alanine, valine, serine, and glycine, respectively. Specifically, the isoleucine at position 163 and the glutamic acid at position 165 may be replaced with alanine-alanine, alanine-valine, serine-valine, or valine-valine, respectively.

In embodiments of the present invention, when various combinations of mutations on the amino acids at positions 163 and 165 of the wild-type ODC were found to lead to increase putrescine productivity, these positions are suggested to be very important in the preparation of the ODC mutant having improved putrescine productivity. In particular, when the amino acids present at the important mutation sites were replaced with small amino acid residues (alanine, serine, valine, or glycine), putrescine productivity was increased.

Further, the modified ODC protein of the present invention may consist of any one amino acid sequence of SEQ ID NO: 34 to SEQ ID NO: 57, and specifically, any one amino acid sequence of SEQ ID NO: 34 to SEQ ID NO: 42, SEQ ID NO: 45, and SEQ ID NO: 49 and SEQ ID NO: 57, which is an amino acid sequence of the modified ODC protein in which isoleucine or glutamic acid at position 163 or 165, respectively, from the N-terminus is replaced with a small residue. The modified ODC protein may include any polypeptide having a homology of 50%, 60%, 70%, 75%, 80%, 85%, 90%, 95%, 97%, or 99% or higher to the above sequences, as long as it has the above modification and superior putrescine conversion activity to that of the wild-type.

As used herein, the term "homology" refers to a percentage of identity between two polynucleotide or polypeptide moieties. Sequence correspondence from one moiety to another may be determined by a known technique in the art. For example, homology may be determined by aligning the sequence information of two polynucleotide molecules or two polypeptide molecules directly by using a computer program that is readily available and capable of aligning sequence information. In addition, homology may be determined by hybridizing the polynucleotides under the condition for forming a stable double-strand in the homologous regions and then digesting the hybridized strand by a single-strand-specific nuclease to determine a size of a digested fragment.

As used herein, the term "homologous" refers to the correlation between proteins where all grammatical forms and spelling variations include superfamily-derived proteins and other species-derived homologous proteins having a "common evolutionary origin". Such proteins (and coding genes thereof) have a sequence homology reflected by a high degree of sequence similarity. However, in general use and in the present invention, when the term "homogeny" is modified by an adjective such as "very high", it refers to a sequence similarity, but not a common evolutionary origin.

As used herein, the term "sequence similarity" refers to the degree of identity or homology among the nucleotide sequences or amino acid sequences of the proteins which may or may not share a common evolutionary origin. In a specific embodiment, when a polypeptide match between two amino acid sequences is least 21% for a fixed length of an amino acid sequence (specifically at least about 50% and most specifically about 75%, 90%, 95%, 96%, 97%, or 99%), those two sequences are "substantially homologous" or "substantially similar". Substantially homologous sequences may be identified by comparing the sequences using standard software used in the data bank or, for example, by performing a Southern hybridization experiment under the stringent conditions defined for a certain system. A defined condition suitable for hybridization is within the scope of conventional techniques in the art (e.g., see Sambrook et al., 1989, infra).

In a specific embodiment of the present invention, structural analysis of the E. coli-derived ODC protein was performed, and based on the structural information, mutagenesis was performed by a rational design strategy. Mutations (V156, D160, I163, E165, Q691) for widening an entrance region of a path for substrate entry into the active site, and mutations (N153, D309) for stabilizing PLP, which is a cofactor binding to the active site, were designed and prepared (Examples 1 and 2). In detail, when isoleucine, as an amino acid at position 163, and glutamic acid, as an amino acid at position 165 from the N-terminus, were replaced with alanine through a modification of replacing the bulky residue at the entrance region of the path with a small residue, alanine, activity of the ODC protein was found to be remarkably increased (Example 3). Meanwhile, ODC proteins having 6 other types of mutants, V156A, D160A, Q691A, N153D, N153E, and D309E, for PLP stabilization, showed very low activity or little activity compared to the wild-type. Therefore, it can be seen that isoleucine at position 163 and glutamic acid at position 165 of an E. coli-derived ODC protein (SEQ ID NO: 1) are important residues that function to increase the protein activity. The mutations were performed by site-directed mutagenesis using primers given in Table 1 and PCR.

Further, in a specific embodiment of the present invention, isoleucine at position 163 and glutamic acid at position 165 were replaced with other small residues, serine, valine, or glycine, in addition to alanine, to optimize modifications of the corresponding residues (Example 4 and Table 4). The respective amino acid residues at positions 163 and 165 were replaced with glycine (G), serine (S), or valine (V). As a result, when the amino acid residue at position 163 was replaced with serine and the amino acid residue at position 165 was replaced with valine, a $kcat/K_M$ value was increased 4.4-fold and 6.9-fold, respectively, compared to the wild-type (Table 5). Based on this result, the two residues were spontaneously changed, and the ODC activity was examined. The activity was increased to 8-fold higher than that of the wild-type by a combination of I163S and E165V, which showed the highest activity on single mutation. One the other hand, the activity was increased to 21.3-fold higher than that of the wild-type by replacement of both of the amino acid residues at positions 163 and 165 to valine (Example 4 and Table 5).

Overall, the increased activities of the ODC enzyme mutants are attributed to an increase in a $kcat/K_M$ value due to an increase in a kcat value, rather than a decrease in a $K_M$ value. It implied that the structure of ODC enzyme is changed to increase a conversion rate into the product, putrescine, rather than the binding affinity of the substrate for the enzyme, ornithine.

In the present invention, the activity of the ODC enzyme is assayed by using a reaction converting ornithine into putrescine. In detail, when ODC enzyme converts one molecule of ornithine into putrescine, one molecule of water is consumed and one molecule of carbon dioxide and one $OH^-$ ion are produced together with putrescine. Therefore, the total pH is increased. When the increased pH is measured at 559 nm using phenol red, a pH indicator, absorbance is increased in proportion to the pH increase during the reaction. This property is used to indirectly measure a production amount of putrescine.

As used herein, the term "ornithine" refers to a basic amino acid which plays an important role in the ornithine cycle, and in particular, L-ornithine is widely found in plants, animals, and microorganisms. In general, ornithine plays an important role in conjunction with the urea cycle in an organism having the ornithine cycle. Further, ornithine may be interconverted to arginine, glutamic acid, and proline in an organism, and it transfers amino groups to α-keto acid and glyoxylic acid. Ornithine is a substrate producing an amine (putrescine) by ornithine decarboxylase, and a polyamine is synthesized therefrom. In the present invention, ornithine may be specifically L-ornithine which may be used as a substrate of ornithine decarboxylase.

As used herein, the term "putrescine" is a substance produced by decarboxylation of ornithine or hydrolysis of agmatine. Putrescine may be found in putrefaction, but also usually found in a normal component in an organism. Putrescine is a polyamine, and functions to constitute ribosomes and to promote cell growth or RNA synthesis. Industrially, putrescine is an important raw material for the production of polyamide-4,6 including nylon-4,6, and studies for its mass production have been continually demanded.

In another aspect, the present invention provides a polynucleotide encoding the modified ODC protein of the present invention.

As used herein, the term "polynucleotide" encompasses DNA and RNA molecules, and a nucleotide as a basic unit of the polynucleotide includes a natural nucleotide as well as an analogue with a modified sugar or base.

In still another aspect, the present invention provides a vector including the polynucleotide encoding the modified ODC protein of the present invention.

As used herein, the term "vector" refers to any carrier for cloning and/or transferring bases to a host cell. A vector may be a replicon to allow for the replication of the fragments combined with other DNA fragments. "Replicon" refers to any genetic unit acting as a self-replicating unit for DNA replication in vivo, that is, replicable by the self-regulation (e.g., plasmid, phage, cosmid, chromosome, and virus). The term "vector" may include viral and non-viral carriers for introducing nucleotides into a host cell in vitro, ex vivo, or in vivo, and it may also include a mini-spherical DNA. For example, the vector may be a plasmid without a bacterial DNA sequence. Removal of bacterial DNA sequences which are rich in CpG area has been conducted to reduce silencing of the transgene expression and to promote continuous expression of a plasmid DNA vector. The term "vector" may also include a transposon or artificial chromosome.

In the present invention, the vector is a vector including the polynucleotide encoding the modified ODC protein of the present invention, and it may be, but is not particularly limited to, a vector capable of replicating and/or expressing the polynucleotide in a eukaryotic or prokaryotic cell including a mammalian cell (e.g., human, monkey, rabbit, rat, hamster, mouse cell, etc.), a plant cell, a yeast cell, an insect cell, or a bacterial cell (e.g., *E. coli*, etc.). Specifically, the vector may be a vector that is operably linked to a proper promoter to allow expression of the polynucleotide in the host cell, and includes at least one selection marker. More specifically, the vector may be in the form in which the polynucleotide is introduced into a phage, plasmid, cosmid, mini-chromosome, virus, or retroviral vector.

A pET system using a T7 promoter generally used in the art is well known, and various expression systems known in the art may be used, but is not limited thereto. In the present invention, specifically, the vector including the polynucleotide encoding the modified ODC protein may be a pET28a vector.

In a specific embodiment of the present invention, the polynucleotide encoding the site-directed modified ODC protein was inserted into the pET28a vector by PCR. Through this process, the modified ODC (speC)-expressing vectors, pET28a-speC_I163A, pET28a-speC_I163G, pET28a-speC_I163S, pET28a-speC_I163V, pET28a-speC_E165A, pET28a-speC_E165S, pET28a-speC_E165G, pET28a-speC_E165V, pET28a-speC_I163A E165A, pET28a-speC_I163S E165V, pET28a-speC_I163A E165V, and pET28a-speC_I163V E165V, were prepared, and the mutations were confirmed by sequence analysis.

In still another aspect, the present invention provides a transformant transformed with the vector.

In the present invention, the transformant is not particularly limited, as long as the modified ODC of the present application is able to express by introducing the vector. The transformant may be bacterial cells such as transformed *E. coli*, *Corynebacterium*, *Streptomyces*, *Salmonella typhimurium*, etc.; yeast cells; fungal cells such as *pichia pastoris*, etc.; insect cells such as *Drosophila*, *Spodoptera* Sf9 cells, etc.; animal cells such as CHO (Chinese hamster ovary cells), SP2/0 (mouse myeloma cells), human lymphoblastoids, COS, NSO (mouse myeloma cells), 293T, Bowes melanoma cells, HT-1080, BHK (baby hamster kidney cells), HEK (human embryonic kidney cells), or PERC.6 (human embryonic retina cells); or plant cells.

In still another aspect, the present invention provides a method of preparing putrescine, the method including the step of reacting L-ornithine, a mixture containing L-ornithine, or an L-ornithine fermentation liquid with the modified ODC protein.

The L-ornithine, modified ODC protein, and putrescine are the same as described above.

In the present invention, a substance reacted with the modified ODC protein for the preparation of putrescine may be L-ornithine, the mixture containing L-ornithine, or the L-ornithine fermentation liquid. The mixture containing L-ornithine refers to a mixture of separately existing L-ornithine and other components, and the L-ornithine fermentation liquid refers to a fermentation liquid in which L-ornithine is produced or its amount is increased during fermentation, and therefore, L-ornithine sufficient for reaction is included, but is not limited thereto.

For example, the method of producing L-ornithine by fermentation and the produced fermentation liquid are disclosed in U.S. Pat. No. 3,668,072, which is herein incorporated by reference (*E. coli*, ATCC 21104).

In the present invention, the modified ODC protein may be a purified modified ODC protein or a microorganism fermentation liquid containing the modified ODC protein. Specifically, the microorganism used in the preparation of the microorganism fermentation liquid may be a microorganism expressing the modified ODC protein of the present invention, and more specifically, it may be a transformant microorganism transformed with a vector including the polynucleotide encoding the modified ODC protein of the present invention.

In still another aspect, the present invention provides a microorganism having improved putrescine productivity, which is prepared by changing to the modified ODC protein in a *Corynebacterium* sp. microorganism having putrescine productivity.

As used herein, the term "microorganism" includes all of a wild-type microorganism and a naturally or artificially genetically modified microorganism, and it may be a microorganism having a particular attenuated or reinforced mechanism due to insertion of a foreign gene or reinforcement or attenuation of activity of an endogenous gene.

As used herein, the term "*Corynebacterium* sp. microorganism having putrescine productivity" refers to a *Corynebacterium* sp. microorganism which has putrescine productivity naturally or by modification. It is already known that putrescine is included in a culture of a *Corynebacterium* sp. microorganism. However, its putrescine productivity is too low, and genes or mechanisms involved in the production have not yet been revealed. Therefore, the "*Corynebacterium* sp. microorganism having putrescine productivity" in the present invention refers to a native strain itself or a *Corynebacterium* sp. microorganism in which a foreign gene involved in the putrescine production mechanism is inserted or activity of an endogenous gene is reinforced or weakened so as to have improved putrescine productivity.

As used herein, the term "*Corynebacterium* sp. microorganism" may be specifically *Corynebacterium glutamicum*, *Corynebacterium ammoniagenes*, *Brevibacterium lactofermentum*, *Brevibacterium flavum*, *Corynebacterium thermoaminogenes*, *Corynebacterium efficiens*, etc., but is not limited thereto. More specifically, the *Corynebacterium* sp. microorganism in the present invention may be *Corynebacterium glutamicum* of which cell growth and survival are hardly affected even when exposed to a high concentration of putrescine. For example, the *Corynebacterium* sp. microorganism may be a *Corynebacterium glutamicum* KCCM11240P (KCCM11138P ΔNCgl1469) strain which is modified to have the weakened NCgl1469 activity compared to the endogenous activity thereof, thereby having improved putrescine productivity, but is not limited thereto. The KCCM11240P strain is a putrescine-overexpressing strain prepared by deleting a gene encoding NCgl1469 in order to block the biosynthetic pathway of N-acetyl putrescine from putrescine, and is disclosed in International Patent Publication No. WO2013/105827.

In a specific embodiment of the present invention, based on the *Corynebacterium* sp. microorganism (KCCM11240P (KCCM11138P ΔNCgl1469)) having improved putrescine productivity by weakening the NCgl1469 activity compared to the endogenous activity thereof, a modified strain was prepared by changing the wild-type speC to an ODC I163S/E165V(speC) mutant having increased putrescine conversion activity in the chromosome (Example 6). The modified strain was designated as *Corynebacterium glutamicum* CC01-0578, and deposited in the Korean Culture Center of Microorganisms (KCCM) on Jun. 10, 2013 with the accession number KCCM11425P under the Budapest Treaty.

In still another aspect, the present invention provides a method of producing putrescine, the method including the steps of culturing the *Corynebacterium* sp. microorganism which has an improved putrescine-producing activity by changing to the modified ODC protein according to the present invention; and recovering putrescine from a culture obtained in the above step.

The *Corynebacterium* sp. microorganism may be specifically *Corynebacterium glutamicum*, and more specifically, a *Corynebacterium glutamicum* CC01-0578 (accession number: KCCM11425P) strain.

As used herein, the term "culture" refers to culturing of a microorganism under artificially controlled environmental conditions. In the present invention, the method of producing putrescine using the *Corynebacterium* sp. microorganism may be conducted using a method widely known in the art. Specifically, examples of the culturing method include a batch process and a fed batch or repeated fed batch process in a continuous manner, but are not limited thereto.

The medium used in the culturing must appropriately satisfy the requirements of specific strains. Culture media for the *Corynebacterium* sp. microorganism are disclosed (e.g., Manual of Methods for General Bacteriology. American Society for Bacteriology. Washington D.C., USA, 1981). As a carbon source in the medium, sugars and carbohydrates such as glucose, sucrose, lactose, fructose, maltose, starch, and cellulose, oils and fats such as soybean oil, sunflower seed oil, castor oil, and coconut oil, fatty acids such as palmitic acid, stearic acid, and linoleic acid, alcohols such as glycerol and ethanol, and organic acids such as acetic acid, etc. may be used. These substances may be used individually or as a mixture. As a nitrogen source, peptone, yeast extract, beef extract, malt extract, corn steep liquor, soybean meal powder, and urea or inorganic compounds such as ammonium sulfate, ammonium chloride, ammonium phosphate, ammonium carbonate, and ammonium nitrate may be used, and these substances may also be used individually or as a mixture. As a phosphorus source, potassium dihydrogen phosphate or dipotassium hydrogen phosphate or the corresponding sodium-containing salt may be used. In addition, the culture medium may include a metal salt such as magnesium sulfate or iron sulfate which is essential for growth, and finally, essential growth-promoting substances such as amino acids and vitamins may be used in addition to the above-mentioned substances. The appropriate precursor may be added to the culture medium. The above substances may be adequately fed into the culture in a batch or continuous manner.

The pH of the culture may be adjusted by a proper basic compound such as sodium hydroxide, potassium hydroxide, or ammonia, or an acidic compound such as phosphoric acid or sulfuric acid. Foaming may be adjusted by an anti-foaming agent such as a fatty acid polyglycol ester. The aerobic condition of the culture may be maintained by introducing oxygen or oxygen-containing gas mixtures (e.g., air). The culturing temperature may be generally 20° C. to 45° C., specifically 25° C. to 40° C. Culturing may be continued until the production of putrescine reaches the desired maximum, and may usually be achieved in 10 hours to 160 hours. Putrescine may be released into the culture medium, or contained in the cell.

The method of producing the putrescine of the present invention includes a step of recovering putrescine from the cell or culture. The method of recovering the putrescine from the cell or culture may be performed using the appropriate known method in the art, for example, centrifugation, filtration, anion exchange chromatography, crystallization, and HPLC, but is not limited thereto.

MODE FOR INVENTION

Hereinafter, the present invention will be described in more detail with reference to Examples. However, these Examples are for illustrative purposes only, and the invention is not intended to be limited. by these Examples.

Example 1. Structural Analysis of ODC (Ornithine Decarboxylase) and Design of Mutant Thereof In general, *E. coli* is known to have two types of ODC. One is an inducible ODC (speF), of which expression is induced at an acidic pH, and the other is a constitutive ODC (spec) involved in the production of a diamine such as putrescine (Applebaum D M, et al., Biochemistry, 16: 1590-1581, 1977). Of these, spec, which is the constitutive ODC involved in the production of putrescine, was selected as a target gene.

Until now, the ODC structures of *Vibrio* and *Lactobacillus* bacteria have been revealed. Of these, *E. coli* ODC (spec) was predicted to have a structure similar to that of *Lactobacillus* 30a ODC. Therefore, based on the 3D structure of *Lactobacillus* ODC, alignment of the amino acid sequence of *E. coli* ODC (spec) was performed using a GeneDoc program (Momany C, et al., J Mol Biol, 4: 849-854, 1995). As a result of comparing the amino acid sequences, sequence identity between *E. coli* speC and *Lactobacillus* 30a ODC was 53% and sequence similarity therebetween was 65%, indicating that the two enzymes are very similar to each other. Therefore, based on the structure of *Lactobacillus* 30a ODC (PDB ID: 1ORD) provided by RCSB Protein Data Bank, homology modeling of the *E. coli* speC structure was performed. As a result, overall skeletons of the proteins were almost identical to each other, and amino acid sequences of the active site involved in binding with PLP (pyridoxal phosphate) were also almost identical to each other.

The result of analyzing the structures of the two enzymes showed that ODC exists as a dimer in cells, the active site thereof is formed at the dimer interface, and the entrance region of a path for a substrate entry into the active site is narrow. Therefore, in order to widen the entrance region for effective entry of the substrate into the active site and rapid conversion of a product, a modification to replace the bulky residues at the entrance region with small residues was designed (V156, D160, 1163, E165, Q691).

Additionally, for stabilization of the cofactor PLP binding to the active site, a mutation for the residues surrounding the active site was also designed (N153, D309).

Example 2. Cloning and Expression of *E. coli* ODC (speC) Gene

To express *E. coli* speC gene, a pET28a (Novagen) vector system generally used in enzyme expression was used. First, the speC gene was amplified by PCR using the chromosome of the wild-type *E. coli* W3110 as a template and primers given in the following Table 1. A gene fragment obtained by PCR amplification and a vector pET28a were treated with restriction enzymes, NdeI and XhoI (37° C., 3 hours), and then the speC gene fragment was inserted into the pET28a vector by a general ligation method.

TABLE 1

| Primer | Primer sequence |
|---|---|
| speC_start (NdeI)_5 (SEQ ID NO: 2) | 5'-cagccatatgaaatcaatga-3' |
| speC_stop (XhoI)_3 (SEQ ID NO: 3) | 5'-ggtgctcgagttacttcaac-3' |

The mutation of the speC expression vector (pET28a-speC) thus prepared was confirmed by sequencing analysis.

The target residues in Example 1 were replaced with a small residue alanine, respectively. To stabilize PLP, the each residues surrounding the active site was modified differently according to the position binding with PLP.

PCR was performed using the prepared pET28a-speC vector as a template and primers given in Table 1 and the following Table 2. First, to mutate the speC gene, primary PCR was performed for the forward (5') and backward (3') regions with respect to the region to be mutated, and then secondary PCR for ligation of two PCR fragments was performed. For example, in the case of speC V156A, the forward region was amplified by PCR using speC_start (NdeI)_5 (SEQ ID NO: 2) and speC_V156A_3 (SEQ ID NO: 5) as primers, and the backward region was amplified by PCR using speC_V156A_5 (SEQ ID NO: 4) and speC_stop (XhoI)_3 (SEQ ID NO: 3) as primers. Secondary PCR was performed using the two PCR fragments obtained by the primary PCR as a template and speC_start (NdeI)_5 (SEQ ID NO: 2) and speC_stop (XhoI)_3 (SEQ ID NO: 3) as primers. The speC_V156A gene finally obtained was inserted into the pET28a vector in the same manner as in the speC gene fragment. Other mutated fragments were also introduced into the pET28a vector by PCR using primers given in Table 2 in the same manner as above, respectively.

Mutations of the speC mutant expression vectors thus prepared (pET28a-speC_V156A, pET28a-speC_D160A, pET28a-speC_I163A, pET28a-speC_E165A, pET28a-speC_Q691A, pET28a-speC_N153D, pET28a-speC_N153E, pET28a-speC_D309E) were confirmed by sequencing analysis.

Example 3. Measurement of an Activity of ODC (speC) Mutant Enzymes 3-1. Preparation of ODC Mutant Enzymes Each of the pET28a-speC mutant vectors prepared in Example 2 was transformed into *E. coli* having DE3 gene type to prepare a strain expressing the ODC enzyme.

Expression of the pET28a-speC mutant vector was performed with reference to a pET system manual (Novagen). In detail, single colonies of respective strains were selected from LB plate media and inoculated into 3 mL of LB liquid medium (+kanamycin 50 μg/mL), followed by incubation at 37° C. and 200 rpm for 16 hours. The culture was re-inoculated into 15 mL of fresh LB medium (+kanamycin 50 μg/mL), and incubated under the same conditions until $OD_{600}$ reached about 0.6. Then, IPTG was immediately added at a final concentration of 0.5 mM and incubated at 18° C. and 180 rpm for 20 hours to induce enzyme expression.

After induction of the enzyme expression, the obtained cells were sonicated and centrifuged. The resulting supernatant was used for a primary activity test. Additionally, to characterize the enzyme, the enzyme was purified and then subjected to a secondary activity test. The enzyme was isolated through a Ni-NTA column using His-tag which was linked to the enzyme in the pET vector. In the purification, a Chelating Excellose spin kit (Bioprogen) was used. ODC (wild-type and mutant speC) enzymes thus obtained were expressed in the soluble form through 8% SDS PAGE, and thus recovered from the supernatant.

3-2. Measurement of an Activity of ODC (speC) Mutant Enzymes

To evaluate putrescine conversion activity by ODC using ornithine as a substrate, activities of ODC (wild-type and

TABLE 2

| Mutation of entrance region | | |
|---|---|---|
| speC_V156A_5 | (SEQ ID NO: 4) | 5'-gctgacgcaaaattgggcgatctgctta-3' |
| speC_V156A_3 | (SEQ ID NO: 5) | 5'-ccaattttgcgtcagcgttacacatatc-3' |
| speC_D160A_5 | (SEQ ID NO: 6) | 5'-attgggcgctctgcttattcatgaagga-3' |
| speC_D160A_3 | (SEQ ID NO: 7) | 5'-aagcagagcgcccaattttacgtcagcg-3' |
| speC_I163A_5 | (SEQ ID NO: 8) | 5'-ctgcttgctcatgaaggatcggcgaaag-3' |
| speC_I163A_3 | (SEQ ID NO: 9) | 5'-ttcatgagcaagcagatcgcccaatttt-3' |
| speC_E165A_5 | (SEQ ID NO: 10) | 5'-attcatgcaggatcggcgaaagatgcgc-3' |
| speC_E165A_3 | (SEQ ID NO: 11) | 5'-cgatcctgcatgaataagcagatcgccc-3' |
| speC_Q691A_5 | (SEQ ID NO: 12) | 5'-gagctggcaggtgtttatagcgaaaccg-3' |
| speC_Q691A_3 | (SEQ ID NO: 13) | 5'-aacacctgccagctccggcgaaaatccc-3' |
| Mutation for PLP stabilization | | |
| speC_N153D_5 | (SEQ ID NO: 14) | 5'-tatgtgtgacgctgacgtaaaattgggc-3' |
| speC_N153D_3 | (SEQ ID NO: 15) | 5'-gtcagcgtcacacatatcggcgcgaaag-3' |
| speC_N153E_5 | (SEQ ID NO: 16) | 5'-tatgtgtgaagctgacgtaaaattgggc-3' |
| speC_N153E_3 | (SEQ ID NO: 17) | 5'-gtcagcttcacacatatcggcgcgaaag-3' |
| speC_D309E_5 | (SEQ ID NO: 18) | 5'-ctgtttgaatccgcgtgggtcggttatgaa-3' |
| speC_D309E_3 | (SEQ ID NO: 19) | 5'-cgcggattcaaacagaatgtaatcacaca-3' | mutant speC) enzymes obtained in Example 3-1 were measured. The ODC activity test to examine putrescine conversion activity was performed with reference to criteria previously reported (Vienozinskiene J, et al., Anal Biochem, 146: 180-183, 1985).

That is, when an ODC enzyme converts one molecule of ornithine into putrescine, one molecule of water is consumed and one molecule of carbon dioxide and one OH⁻ ion are produced together with putrescine. Therefore, total pH is increased (Reaction Scheme 1). When the increased pH is measured at 559 nm using phenol red, a pH indicator, absorbance is changed. The absorbance is increased in proportion to the pH increase. An amount of putrescine was indirectly measured by using this property.

$$\text{L-ornithine} + H_2O \rightarrow \text{putrescine} + CO_2 + OH^-$$ [Reaction Scheme 1]

For a primary activity test of the ODC enzymes, an amount of total protein in supernatants before purification was quantified and concentrations of supernatants were adjusted equally. The reaction solution was prepared using 30 µg of enzyme supernatant, 10 mM ornithine, and 1.25 µM PLP, and then 40 µM phenol red was used to monitor pH change.

As a result of the activity measurement, the activity of I163A and E165A of the ODC mutant enzymes showed a higher putrescine production rate than that of the wild-type. The activity of remaining 6 types of ODC mutants, V156A, D160A, Q691A, N153D, N153E, and D309E, showed little changes in absorbance at 559 nm (see FIG. 1).

To characterize the two ODC mutant enzymes, I163A and E165A, which were selected in the primary screening, these were purified with His-tag and quantified, and then a rate of putrescine conversion according to ornithine concentration was measured. The ODC enzyme was used at a concentration of 10 µg, and ornithine was used at a concentration of 0.15 mM to 10 mM. In this range, pH change was measured using phenol red.

TABLE 3

| ODC enzyme | $K_M$ (mM) | kcat (sec⁻¹) | $\text{kcat}/K_M$ (sec⁻¹M⁻¹) | Fold (kcat/$K_M$) |
|---|---|---|---|---|
| WT (wild-type) | 1.5 | 1.6 | 1.1 × 10³ | 1.0 |
| I163A mutant | 0.7 | 1.8 | 2.6 × 10³ | 2.4 |
| E165A mutant | 1.1 | 2.4 | 2.2 × 10³ | 2.0 |

These results showed that the modified ODC enzymes, I163A and E165A, designed through the ODC structural analysis showed 53% and 27% reductions in the $K_M$ value compared to the wild-type, respectively, indicating that their binding affinities for the substrate ornithine were increased. Further, the activity of the modified ODC I163A and E165A showed 12.5% and 50% increases in the kcat value compared to WT, respectively, indicating that the ability to convert ornithine into putrescine was also increased. Finally, the kcat/$K_M$ value showing the characteristic of the enzyme activity was calculated. I163A and E165A showed 2.4- and 2-fold increases in the kcat/$K_M$ value compared to WT, respectively (Table 3).

Example 4. Optimization of ODC (speC) Mutation

As confirmed in Example 3, mutations of a variety of small amino acid residues at the amino acid (isoleucine) at position 163 and the amino acid (glutamic acid) at position 165, which are important residues in ODC activity, were performed. The mutations were performed in the same manner as in Example 1, and primers used therein are given in the following Table 4. Additionally, single mutations were performed into the positions 163 and 165, respectively and then double mutants were prepared by introducing each position with a mutation combination showing increased ODC activity, followed by evaluation.

TABLE 4

| Primer | Primer sequence |
|---|---|
| speC_I163G_5 (SEQ ID NO: 20) | 5'-ctgcttggtcatgaaggatcggcgaaagat-3' |
| speC_I163G_3 (SEQ ID NO: 21) | 5'-ttcatgaccaagcagatcgcccaatttt-3' |
| speC_I163S_5 (SEQ ID NO: 22) | 5'-ctgctttctcatgaaggatcggcgaaagat-3' |
| speC_I163S_3 (SEQ ID NO: 23) | 5'-ttcatgagaaagcagatcgcccaatttt-3' |
| speC_I163V_5 (SEQ ID NO: 24) | 5'-ctgcttgttcatgaaggatcggcgaaagat-3' |
| speC_I163V_3 (SEQ ID NO: 25) | 5'-ttcatgaacaagcagatcgcccaatttt-3' |
| speC_E165G_5 (SEQ ID NO: 26) | 5'-attcatggaggatcggcgaaagatgcgc-3' |
| speC_E165G_3 (SEQ ID NO: 27) | 5'-cgatcctccatgaataagcagatcgccc-3' |
| speC_E165S_5 (SEQ ID NO: 28) | 5'-attcattcaggatcggcgaaagatgcgc-3' |
| speC_E165S_3 (SEQ ID NO: 29) | 5'-cgatcctgaatgaataagcagatcgccc-3' |
| speC_E165V_5 (SEQ ID NO: 30) | 5'-attcatgtaggatcggcgaaagatgcgc-3' |

TABLE 4-continued

| Primer | Primer sequence |
|---|---|
| speC_E165V_3 (SEQ ID NO: 31) | 5'-cgatcctacatgaataagcagatcgccc-3' |

ODC mutants prepared by using the primers of Table 4 were purified according to the method of Examples 2 and 3 and the rates of putrescine conversion were measured. The results of measuring the rates of putrescine conversion of the prepared ODC mutants are given in the following Table 5.

TABLE 5

| ODC enzyme | $K_M$ (mM) | kcat (sec$^{-1}$) | kcat/$K_M$ (sec$^{-1}$M$^{-1}$) | Fold (kcat/$K_M$) |
|---|---|---|---|---|
| WT (wild-type) | 1.5 | 1.6 | $1.1 \times 10^3$ | 1.0 |
| I163G mutant | 1.7 | 4.2 | $2.5 \times 10^3$ | 2.3 |
| I163S mutant | 1.5 | 7.4 | $4.8 \times 10^3$ | 4.4 |
| I163V mutant | 1.3 | 4.4 | $3.5 \times 10^3$ | 3.2 |
| E165G mutant | 3.0 | 5.6 | $1.9 \times 10^3$ | 1.7 |
| E165S mutant | 1.9 | 10.1 | $5.2 \times 10^3$ | 4.7 |
| E165V mutant | 1.4 | 10.9 | $7.6 \times 10^3$ | 6.9 |
| I163A E165A mutant | 1.5 | 6.4 | $4.1 \times 10^3$ | 3.7 |
| I163S E165V mutant | 1.2 | 10.5 | $8.8 \times 10^3$ | 8.0 |
| I163A E165V mutant | 0.9 | 6.3 | $6.8 \times 10^3$ | 6.2 |
| I163V E165V mutant | 1.1 | 25.7 | $2.3 \times 10^3$ | 21.3 |

As shown in Table 5, when the amino acid residues 163 and 165 were introduced with single mutations of glycine (G), serine (S), and valine (V), respectively, replacement of the residue 163 with serine and replacement of the residue 165 with valine showed 4.4- and 6.9-fold increases in the kcat/$K_M$ value compared to the wild-type, respectively. Based on this result, double mutations were introduced into the two residues, and their activities were examined. Surprisingly, not a double mutation of I163S and E165V combination, each single mutation showing the highest activity, but a double mutation of replacement of both 163 and 165 residues with valine showed a 21.3-fold increase in the activity compared to the wild-type.

Overall, the increased activities of the ODC enzyme mutants were attributed to an increase in a kcat/$K_M$ value due to an increase in a kcat value, rather than a decrease in a $K_M$ value, implying that the ODC enzyme is mutated to have a structure increasing a conversion rate into the product putrescine rather than a structure increasing the binding affinity of the substrate ornithine for the enzyme.

Example 5. Preparation of ODC Mutant Enzyme-Expressing Strain Using Ornithine as Substrate and Measurement of Putrescine Conversion It was evaluated whether the ODC mutant enzymes in which mutations are optimized in Example 4 practically influence on conversion of ornithine into putrescine in a microorganism.

In detail, strains prepared by introducing E. coli having a DE3 genetic type with the prepared pET28a-speC mutant vectors were used to perform the experiment. Single colonies of respective strains were selected from LB plate media and inoculated into 3 mL of LB liquid medium (+kanamycin 50 µg/mL), followed by incubation at 37° C. and 200 rpm for 16 hours. The culture was re-inoculated into 25 mL of fresh LB medium (+kanamycin 50 µg/mL and 0.2% glucose), and incubated until $OD_{600}$ reached 0.5 to 0.6. Then, 0.5 mM IPTG was added to induce ODC (spec) expression, and incubated at 18° C. and 200 rpm for 20 hours. Then, centrifugation was performed to discard the supernatant and to collect cells. The cells obtained in the form of a pellet were resuspended in 1×M9 minimal medium (3.37 mM $Na_2HPO_4$, 2.2 mM $KH_2PO_4$, 0.86 mM NaCl, 0.94 mM $NH_4Cl$) to adjust an $OD_{600}$ value to 20. Additionally, 10 mM ornithine as a substrate and 0.5 µM PLP as a cofactor were added to a final volume of 10 mL. The reaction was allowed under conditions of 25° C. and 200 rpm with shaking, and sampling was performed over time. The concentration of the converted putrescine was measured by a method of quantifying putrescine using TNBS (Ngo T T, et al., Anal Biochem, 160: 290-293, 1987).

In the TNBS method, the supernatant obtained by centrifugation of the sampled culture was diluted 50-fold and used to perform the analysis. 1 mL of 4 N NaOH was added to 0.5 mL of the diluted sample, and then 2 mL of 1-pentanol was further added and mixed well. Centrifugation was performed at 2000 rpm for 5 minutes, and then 1 mL of the supernatant was added to a new tube containing 1 mL of 0.1 M $Na_2B_4O_7$ (pH 8.0), and these were mixed well. 1 mL of 10 mM TNBS was further added and mixed well, and 2 mL of DMSO was added thereto and mixed. Then, centrifugation was performed, and absorbance of the resulting supernatant was measured at 426 nm.

TABLE 6

| | 0 hr | | 2 hr | | 4 hr | |
|---|---|---|---|---|---|---|
| | put (mM) | Conversion rate (%) | put (mM) | Conversion rate (%) | put (mM) | Conversion rate (%) |
| WT wild-type | 1.6 | 16 | 5.7 | 57 | 8.6 | 86 |
| I163V mutant | 1.5 | 15 | 7.5 | 75 | 9.8 | 98 |
| E165V mutant | 1.6 | 16 | 7.9 | 79 | 10.1 | 100 |
| I163V E165V mutant | 1.6 | 16 | 7.7 | 77 | 10.0 | 100 |

Putrescine conversion of the wild-type and 3 types of the ODC mutants were measured. As a result, the ODC mutants showed about 32% to 39% increased conversion rates of ornithine into putrescine in the sample collected at 2 hours compared to the wild-type. There was little difference in the conversion rate between the ODC mutations, and they showed no difference in the activity in which the purified ODC mutants showed a great difference in an in vitro experiment. However, the wild-type showed incomplete reaction even after 4 hours, whereas the mutants showed almost complete reaction within 4 hours. As a result, the increased activities of the ODC mutants were also confirmed in the enzyme conversion strains in vivo.

Example 6. Preparation of, Putrescine-Producing Strain Having ODC Mutant and Measurement of Putrescine Productivity In order to examine whether the putrescine productivity is affected when the ODC mutants having increased putrescine conversion activity are practically introduced into the putrescine-producing strain, putrescine productivity was measured.

6-1. Preparation of Putrescine-Producing Strain Having ODC Mutant

Based on the *Corynebacterium* sp. microorganism (KCCM11240P) which has improved putrescine productivity by weakening the NCgl1469 activity compared to the endogenous activity thereof, a mutant strain was prepared by changing the wild-type speC to the ODC (spec) having increased putrescine conversion activity in the chromosome. The *Corynebacterium glutamicum* (KCCM11240P) strain having improved putrescine productivity is a strain disclosed in International Patent Publication No. WO2013/105827, and it was prepared using a *Corynebacterium* sp. microorganism (KCCM11138P) having putrescine productivity as a mother strain, disclosed in International Patent Publication No. WO2012/077995. In more detail, the strain was prepared by cloning the N-terminal and C-terminal regions of NCgl1469 into a pDZ vector, based on the base sequence of NCgl1469 gene of ATCC13032 strain, introducing the vector into a *Corynebacterium* sp. microorganism (KCCM11138P) having putrescine productivity by electroporation, and then plating the strain on a medium containing kanamycin (25 μg/mL), followed by selection. Successful chromosomal insertion of the vector was confirmed by selecting blue colonies on a medium containing X-gal (5-bromo-4-chloro-3-indolyl-β-D-galactopyranoside). The primary chromosome-inserted strain was cultured in a nutrient medium, followed by spreading the diluted strain on a medium containing X-gal and no antibiotic and selecting white colonies which appeared at a relatively low ratio. Finally, an NCgl1469 gene-deleted strain was selected by crossover. The final KCCM11138P ΔNCgl1469 strain thus prepared is a putrescine-overexpressing strain having improved putrescine productivity compared to the mother strain KCCM11138P, the KCCM11138P ΔNCgl1469 strain having a deletion of the gene encoding NCgl1469, which is a protein involved in a pathway of decomposing putrescine into N-acetyl putrescine in cells.

In detail, DNA fragments of the ODC (spec) mutants prepared in Examples 2 and 4 was amplified using speC_start (BamHI)_5 and speC_stop (XbaI)_3 primers given in the following Table 7. Specifically, the prepared pET28a-speC mutant (I163S, I163V, I163S E165V) vectors as templates and two primers of speC_start (BamHI)_5 and speC_stop (XbaI)_3 given in the following Table 7 were used to perform PCR.

The gene fragments obtained by PCR and a vector pDZ were treated with restriction enzymes, BamHI and XbaI (37° C., 3 hours), and then the gene fragments of the speC mutants were inserted into the pDZ vector by a general ligation method, respectively. The recombinant vectors for chromosomal insertion (pDZ-speC_I163S, pDZ-speC_I163V, pDZ-speC_I163S E165V) thus prepared were confirmed by sequencing analysis.

To obtain strains in which the speC mutants were inserted into the chromosome, each of the prepared pDZ-speC_I163S, pDZ-speC_I163V, and pDZ-speC_I163S E165V recombinant vectors was transformed into the KCCM11240P strain by electroporation, and then spread on BHIS plate medium (37 g/L of brain heart infusion, 91 g/L of sorbitol, and 2% agar per 1 L+25 μg/mL of kanamycin).

Successful chromosomal insertion of the vector was determined by examining appearance of blue colonies on a solid medium containing X-gal (5-bromo-4-chloro-3-indolyl-3-D-galactopyranoside). The primary chromosome-inserted strain was cultured in a nutrient medium with shaking (30° C., 8 hours), followed by serial dilution and spreading on the solid medium containing X-gal. Most colonies were blue, whereas white colonies appeared at a relatively low ratio. From the selected colonies, strains having speC mutants in the chromosome by secondary crossover were finally obtained. These strains were finally identified by sequencing analysis of the mutants. The identified strains were designated as KCCM11240P::speC_I163S, KCCM11240P::speC_I163V, and KCCM11240P::speC_I163S E165V. Of these, KCCM11240P::speC_I163S E165V was designated as *Corynebacterium glutamicum* CC01-0578 and deposited in the Korean Culture Center of Microorganisms (KCCM) on Jun. 10, 2013 with the accession number KCCM11425P under the Budapest Treaty.

6-2. Measurement of Putrescine Productivity of Putrescine-Producing Strain Having ODC Mutant In order to examine the effect of ODC (speC) mutant on the putrescine productivity of the putrescine-producing strain, the strains prepared in Example 6-1 were evaluated for putrescine productivity.

In detail, the prepared strains were cultured in CM plate medium containing 1 mM arginine (1% glucose, 1% polypeptone, 0.5% yeast extract, 0.5% beef extract, 0.25% NaCl, 0.2% urea, 100 μL of 50% NaOH, 2% agar, pH 6.8 per 1 L) at 30° C. for 16 hours, and then a loop of cell culture was inoculated in 25 mL of titer medium of the following Table 8, and cultured with shaking at 200 rpm at 30° C. for 24 hours. All of the prepared strains were cultured with addition of 1 mM arginine in the medium during fermentation.

TABLE 8

| Component | Concentration/content (per 1 L) |
| --- | --- |
| Glucose | 8% |
| Soybean protein | 0.25% |
| Corn steep solids | 0.5% |

TABLE 7

| Primer | Primer sequence |
| --- | --- |
| speC_start (BamHI)_5 (SEQ ID NO: 32) | 5'-cgcggatccatgaaatcaatgaatattgc-3' |
| speC_stop (XbaI)_3 (SEQ ID NO: 33) | 5'-gctctacattacttcaacacataaccgt-3' |

TABLE 8-continued

| Component | Concentration/content (per 1 L) |
| --- | --- |
| $(NH_4)_2SO_4$ | 4% |
| Urea | 0.15% |
| $KH_2PO_4$ | 0.1% |
| $MgSO_4 \cdot 7H_2O$ | 0.05% |
| Biotin | 100 μg |
| Thiamine hydrochloride | 3000 μg |
| Calcium-panthotenic acid | 3000 μg |
| Nicotinamide | 3000 μμg |
| $CaCO_3$ | 5% |

As shown in Table 9, each strain introduced with the ODC (spec) mutant having improved activity showed a 37% to 105% increase in the putrescine production at 24 hours.

These results show that the putrescine-producing strain having the ODC mutant is able to produce a high concentration of putrescine with respect to the sugar consumption compared to the known strain.

TABLE 9

| | 12 hours | |
| --- | --- | --- |
| Strain | Put (g/L) | Fold (%) |
| KCCM11240P | 1.3 | 100 |
| KCCM11240P I163S mutant strain | 2.7 | 205 |
| KCCM11240P E165V mutant strain | 2.7 | 193 |
| KCCM11240P I163S E165V mutant strain | 1.8 | 137 |

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds, are therefore intended to be embraced by the claims.

The invention claimed is:

1. A recombinant microorganism with an improved putrescine-producing ability, comprising a modified ornithine decarboxylase (ODC) protein having an amino acid sequence at least 95% identical to SEQ ID NO: 1, wherein an isoleucine at the position corresponding to position 163 of SEQ ID NO: 1 is replaced with an amino acid residue other than isoleucine, and/or a glutamic acid at the position corresponding to position 165 of SEQ ID NO: 1 is replaced with an amino acid residue other than glutamic acid.

2. The recombinant microorganism according to claim 1, wherein the glutamic acid at the position corresponding to position 165 of SEQ ID NO:1 is replaced with alanine, glycine, serine, or valine.

3. The recombinant microorganism according to claim 1, wherein the isoleucine at the position corresponding to at position 163 of SEQ ID NO:1 is replaced with alanine, glycine, serine, or valine.

4. The recombinant microorganism according to claim 1, wherein (a) the amino acid at a position corresponding to position 163 of SEQ ID NO: 1 is replaced with alanine and the amino acid at a position corresponding to position 165 of SEQ ID NO: 1 is replaced with alanine, (b) the amino acid at a position corresponding to position 163 of SEQ ID NO: 1 is replaced with alanine and the amino acid at a position corresponding to position 165 of SEQ ID NO: 1 is replaced with valine, (c) the amino acid at a position corresponding to position 163 of SEQ ID NO: 1 is replaced with serine and the amino acid at a position corresponding to position 165 of SEQ ID NO: 1 is replaced with valine, or (d) the amino acid at a position corresponding to position 163 of SEQ ID NO: 1 is replaced with valine and the amino acid at a position corresponding to position 165 of SEQ ID NO: 1 is replaced with valine.

5. The recombinant microorganism according to claim 1, wherein the modified ODC protein comprises an amino acid sequence selected from the group consisting of SEQ ID NOs: 34 to 57.

6. The recombinant microorganism according to claim 1, wherein the microorganism is selected from the group consisting of a *Corynebacterium* sp. microorganism, an *Escherichia* sp. microorganism, and a *Lactobacillus* sp. microorganism.

7. The recombinant microorganism according to claim 1, wherein the microorganism is a *Corynebacterium* sp. microorganism.

8. A method of producing putrescine, comprising the steps of:
(a) culturing the microorganism according to claim 1 in a medium; and
(b) recovering putrescine from a culture obtained in step (a).

9. A method of producing putrescine, comprising the steps of:
(a) culturing the microorganism according to claim 2 in a medium; and
(b) recovering putrescine from a culture obtained in step (a).

10. A method of producing putrescine, comprising the steps of:
(a) culturing the microorganism according to claim 3 in a medium; and
(b) recovering putrescine from a culture obtained in step (a).

11. A method of producing putrescine, comprising the steps of:
(a) culturing the microorganism according to claim 4 in a medium; and
(b) recovering putrescine from a culture obtained in step (a).

12. A method of producing putrescine, comprising the steps of:
(a) culturing the microorganism according to claim 5 in a medium; and
(b) recovering putrescine from a culture obtained in step (a).

13. A method of producing putrescine, comprising the steps of:
(a) culturing the microorganism according to claim 6 in a medium; and
(b) recovering putrescine from a culture obtained in step (a).

14. A method of producing putrescine, comprising the steps of:
(a) culturing the microorganism according to claim 7 in a medium; and
(b) recovering putrescine from a culture obtained in step (a).

* * * * *

SEQUENCE LISTING

```
<160> NUMBER OF SEQ ID NOS: 57

<210> SEQ ID NO 1
<211> LENGTH: 711
<212> TYPE: PRT
<213> ORGANISM: Escherichia coli

<400> SEQUENCE: 1

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
                20                  25                  30

Val Ala Ala Val Val Ile Thr Ala Ala Asp Ser Arg Ser Gly Ile Leu
            35                  40                  45

Ala Leu Leu Lys Arg Thr Gly Phe His Leu Pro Val Phe Leu Tyr Ser
        50                  55                  60

Glu His Ala Val Glu Leu Pro Ala Gly Val Thr Ala Val Ile Asn Gly
    65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125

Phe Lys Lys His Pro Ala Gly Arg His Phe Tyr Asp Phe Phe Gly Glu
    130                 135                 140

Asn Val Phe Arg Ala Asp Met Cys Asn Ala Asp Val Lys Leu Gly Asp
145                 150                 155                 160

Leu Leu Ile His Glu Gly Ser Ala Lys Asp Ala Gln Lys Phe Ala Ala
                165                 170                 175

Lys Val Phe His Ala Asp Lys Thr Tyr Phe Val Leu Asn Gly Thr Ser
            180                 185                 190

Ala Ala Asn Lys Val Val Thr Asn Ala Leu Leu Thr Arg Gly Asp Leu
        195                 200                 205

Val Leu Phe Asp Arg Asn Asn His Lys Ser Asn His His Gly Ala Leu
    210                 215                 220
```

```
Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
            245                 250                 255

Leu Arg Gln Gln Ile Arg Asp Val Ala Pro Glu Lys Ala Asp Leu Pro
        260                 265                 270

Arg Pro Tyr Arg Leu Ala Ile Ile Gln Leu Gly Thr Tyr Asp Gly Thr
    275                 280                 285

Val Tyr Asn Ala Arg Gln Val Ile Asp Thr Val Gly His Leu Cys Asp
290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Ala Gly Phe
        340                 345                 350

Ser Gln Thr Ser Gln Ile His Lys Lys Asp Asn His Ile Arg Gly Gln
        355                 360                 365

Ala Arg Phe Cys Pro His Lys Arg Leu Asn Asn Ala Phe Met Leu His
370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
            405                 410                 415

Val Glu Ile Gly Ile Glu Ala Arg Lys Ala Ile Leu Ala Arg Cys Lys
        420                 425                 430

Leu Phe Arg Pro Phe Ile Pro Pro Val Val Asp Gly Lys Leu Trp Gln
    435                 440                 445

Asp Tyr Pro Thr Ser Val Leu Ala Ser Asp Arg Arg Phe Phe Ser Phe
    450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
            485                 490                 495

Ala Glu Thr Gly Glu Tyr Ser Asp Phe Gly Val Pro Ala Thr Ile Leu
        500                 505                 510

Ala His Tyr Leu Arg Glu Asn Gly Ile Val Pro Glu Lys Cys Asp Leu
        515                 520                 525

Asn Ser Ile Leu Phe Leu Leu Thr Pro Ala Glu Ser His Glu Lys Leu
530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
            565                 570                 575

Val Arg Tyr Arg Asp Tyr Thr Leu Arg Gln Leu Cys Gln Glu Met His
        580                 585                 590

Asp Leu Tyr Val Ser Phe Asp Val Lys Asp Leu Gln Lys Ala Met Phe
        595                 600                 605

Arg Gln Gln Ser Phe Pro Ser Val Val Met Asn Pro Gln Asp Ala His
    610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
```

```
                    645                 650                 655
Leu Cys Val Val Pro Gly Glu Val Trp Gly Gly Ala Val Gln Arg Tyr
                660                 665                 670

Phe Leu Ala Leu Glu Glu Gly Val Asn Leu Leu Pro Gly Phe Ser Pro
            675                 680                 685

Glu Leu Gln Gly Val Tyr Ser Glu Thr Asp Ala Asp Gly Val Lys Arg
    690                 695                 700

Leu Tyr Gly Tyr Val Leu Lys
705                 710

<210> SEQ ID NO 2
<211> LENGTH: 20
<212> TYPE: DNA
<213> ORGANISM: Artificial Sequence
<220> FEATURE:
<223> OTHER INFORMATION: speC_start (NdeI)_5 Primer

<400> SEQUENCE: 2
cagccatatg aaatcaatga                                             20

<210> SEQ ID NO 3
<211> LENGTH: 20
<212> TYPE: DNA
<213> ORGANISM: Artificial Sequence
<220> FEATURE:
<223> OTHER INFORMATION: speC_stop (XhoI)_3 Primer

<400> SEQUENCE: 3
ggtgctcgag ttacttcaac                                             20

<210> SEQ ID NO 4
<211> LENGTH: 28
<212> TYPE: DNA
<213> ORGANISM: Artificial Sequence
<220> FEATURE:
<223> OTHER INFORMATION: speC_V156A_5 Primer

<400> SEQUENCE: 4
gctgacgcaa aattgggcga tctgctta                                    28

<210> SEQ ID NO 5
<211> LENGTH: 28
<212> TYPE: DNA
<213> ORGANISM: Artificial Sequence
<220> FEATURE:
<223> OTHER INFORMATION: speC_V156A_3 Primer

<400> SEQUENCE: 5
ccaattttgc gtcagcgtta cacatatc                                    28

<210> SEQ ID NO 6
<211> LENGTH: 28
<212> TYPE: DNA
<213> ORGANISM: Artificial Sequence
<220> FEATURE:
<223> OTHER INFORMATION: speC_D160A_5 primer

<400> SEQUENCE: 6
attgggcgct ctgcttattc atgaagga                                    28

<210> SEQ ID NO 7
<211> LENGTH: 28
<212> TYPE: DNA
<213> ORGANISM: Artificial Sequence
```

<220> FEATURE:
<223> OTHER INFORMATION: speC_D160A_3 primer

<400> SEQUENCE: 7
aagcagagcg cccaatttta cgtcagcg                28

<210> SEQ ID NO 8
<211> LENGTH: 28
<212> TYPE: DNA
<213> ORGANISM: Artificial Sequence
<220> FEATURE:
<223> OTHER INFORMATION: speC_I163A_5 primer

<400> SEQUENCE: 8
ctgcttgctc atgaaggatc ggcgaaag                28

<210> SEQ ID NO 9
<211> LENGTH: 28
<212> TYPE: DNA
<213> ORGANISM: Artificial Sequence
<220> FEATURE:
<223> OTHER INFORMATION: speC_I163A_3 primer

<400> SEQUENCE: 9
ttcatgagca agcagatcgc ccaatttt                28

<210> SEQ ID NO 10
<211> LENGTH: 28
<212> TYPE: DNA
<213> ORGANISM: Artificial Sequence
<220> FEATURE:
<223> OTHER INFORMATION: speC_E165A_5 primer

<400> SEQUENCE: 10
attcatgcag gatcggcgaa agatgcgc                28

<210> SEQ ID NO 11
<211> LENGTH: 28
<212> TYPE: DNA
<213> ORGANISM: Artificial Sequence
<220> FEATURE:
<223> OTHER INFORMATION: speC_E165A_3 primer

<400> SEQUENCE: 11
cgatcctgca tgaataagca gatcgccc                28

<210> SEQ ID NO 12
<211> LENGTH: 28
<212> TYPE: DNA
<213> ORGANISM: Artificial Sequence
<220> FEATURE:
<223> OTHER INFORMATION: speC_Q691A_5 primer

<400> SEQUENCE: 12
gagctggcag gtgtttatag cgaaaccg                28

<210> SEQ ID NO 13
<211> LENGTH: 28
<212> TYPE: DNA
<213> ORGANISM: Artificial Sequence
<220> FEATURE:
<223> OTHER INFORMATION: speC_Q691A_3 primer

<400> SEQUENCE: 13
aacacctgcc agctccggcg aaaatccc                28

<210> SEQ ID NO 14
<211> LENGTH: 28
<212> TYPE: DNA
<213> ORGANISM: Artificial Sequence
<220> FEATURE:
<223> OTHER INFORMATION: speC_N153D_5 primer

<400> SEQUENCE: 14
tatgtgtgac gctgacgtaa aattgggc                                       28

<210> SEQ ID NO 15
<211> LENGTH: 28
<212> TYPE: DNA
<213> ORGANISM: Artificial Sequence
<220> FEATURE:
<223> OTHER INFORMATION: speC_N153D_3 primer

<400> SEQUENCE: 15
gtcagcgtca cacatatcgg cgcgaaag                                       28

<210> SEQ ID NO 16
<211> LENGTH: 28
<212> TYPE: DNA
<213> ORGANISM: Artificial Sequence
<220> FEATURE:
<223> OTHER INFORMATION: speC_N153E_5 primer

<400> SEQUENCE: 16
tatgtgtgaa gctgacgtaa aattgggc                                       28

<210> SEQ ID NO 17
<211> LENGTH: 28
<212> TYPE: DNA
<213> ORGANISM: Artificial Sequence
<220> FEATURE:
<223> OTHER INFORMATION: speC_N153E_3 primer

<400> SEQUENCE: 17
gtcagcttca cacatatcgg cgcgaaag                                       28

<210> SEQ ID NO 18
<211> LENGTH: 30
<212> TYPE: DNA
<213> ORGANISM: Artificial Sequence
<220> FEATURE:
<223> OTHER INFORMATION: speC_D309E_5 primer

<400> SEQUENCE: 18
ctgtttgaat ccgcgtgggt cggttatgaa                                     30

<210> SEQ ID NO 19
<211> LENGTH: 29
<212> TYPE: DNA
<213> ORGANISM: Artificial Sequence
<220> FEATURE:
<223> OTHER INFORMATION: speC_D309E_3 primer

<400> SEQUENCE: 19
cgcggattca aacagaatgt aatcacaca                                      29

<210> SEQ ID NO 20
<211> LENGTH: 30
<212> TYPE: DNA
<213> ORGANISM: Artificial Sequence
<220> FEATURE:
<223> OTHER INFORMATION: speC_I163G_5 primer

```
<400> SEQUENCE: 20
ctgcttggtc atgaaggatc ggcgaaagat                                          30

<210> SEQ ID NO 21
<211> LENGTH: 28
<212> TYPE: DNA
<213> ORGANISM: Artificial Sequence
<220> FEATURE:
<223> OTHER INFORMATION: speC_I163G_3 primer

<400> SEQUENCE: 21
ttcatgacca agcagatcgc ccaatttt                                            28

<210> SEQ ID NO 22
<211> LENGTH: 30
<212> TYPE: DNA
<213> ORGANISM: Artificial Sequence
<220> FEATURE:
<223> OTHER INFORMATION: speC_I163S_5 primer

<400> SEQUENCE: 22
ctgctttctc atgaaggatc ggcgaaagat                                          30

<210> SEQ ID NO 23
<211> LENGTH: 28
<212> TYPE: DNA
<213> ORGANISM: Artificial Sequence
<220> FEATURE:
<223> OTHER INFORMATION: speC_I163S_3 primer

<400> SEQUENCE: 23
ttcatgagaa agcagatcgc ccaatttt                                            28

<210> SEQ ID NO 24
<211> LENGTH: 30
<212> TYPE: DNA
<213> ORGANISM: Artificial Sequence
<220> FEATURE:
<223> OTHER INFORMATION: speC_I163V_5 primer

<400> SEQUENCE: 24
ctgcttgttc atgaaggatc ggcgaaagat                                          30

<210> SEQ ID NO 25
<211> LENGTH: 28
<212> TYPE: DNA
<213> ORGANISM: Artificial Sequence
<220> FEATURE:
<223> OTHER INFORMATION: speC_I163V_3 primer

<400> SEQUENCE: 25
ttcatgaaca agcagatcgc ccaatttt                                            28

<210> SEQ ID NO 26
<211> LENGTH: 28
<212> TYPE: DNA
<213> ORGANISM: Artificial Sequence
<220> FEATURE:
<223> OTHER INFORMATION: speC_E165G_5 primer

<400> SEQUENCE: 26
attcatggag gatcggcgaa agatgcgc                                            28

<210> SEQ ID NO 27
```

<210> SEQ ID NO 27
<211> LENGTH: 28
<212> TYPE: DNA
<213> ORGANISM: Artificial Sequence
<220> FEATURE:
<223> OTHER INFORMATION: speC_E165G_3 primer

<400> SEQUENCE: 27
cgatcctcca tgaataagca gatcgccc                                28

<210> SEQ ID NO 28
<211> LENGTH: 28
<212> TYPE: DNA
<213> ORGANISM: Artificial Sequence
<220> FEATURE:
<223> OTHER INFORMATION: speC_E165S_5 primer

<400> SEQUENCE: 28
attcattcag gatcggcgaa agatgcgc                                28

<210> SEQ ID NO 29
<211> LENGTH: 28
<212> TYPE: DNA
<213> ORGANISM: Artificial Sequence
<220> FEATURE:
<223> OTHER INFORMATION: speC_E165S_3 primer

<400> SEQUENCE: 29
cgatcctgaa tgaataagca gatcgccc                                28

<210> SEQ ID NO 30
<211> LENGTH: 28
<212> TYPE: DNA
<213> ORGANISM: Artificial Sequence
<220> FEATURE:
<223> OTHER INFORMATION: speC_E165V_5 primer

<400> SEQUENCE: 30
attcatgtag gatcggcgaa agatgcgc                                28

<210> SEQ ID NO 31
<211> LENGTH: 28
<212> TYPE: DNA
<213> ORGANISM: Artificial Sequence
<220> FEATURE:
<223> OTHER INFORMATION: speC_E165V_3 primer

<400> SEQUENCE: 31
cgatcctaca tgaataagca gatcgccc                                28

<210> SEQ ID NO 32
<211> LENGTH: 29
<212> TYPE: DNA
<213> ORGANISM: Artificial Sequence
<220> FEATURE:
<223> OTHER INFORMATION: speC_start (BamHI)_5 primer

<400> SEQUENCE: 32
cgcggatcca tgaaatcaat gaatattgc                               29

<210> SEQ ID NO 33
<211> LENGTH: 28
<212> TYPE: DNA
<213> ORGANISM: Artificial Sequence
<220> FEATURE:
<223> OTHER INFORMATION: speC_stop (XbaI)_3 primer

<400> SEQUENCE: 33
gctctacatt acttcaacac ataaccgt					28

<210> SEQ ID NO 34
<211> LENGTH: 711
<212> TYPE: PRT
<213> ORGANISM: Artificial Sequence
<220> FEATURE:
<223> OTHER INFORMATION: Modified ODC protein I163A

<400> SEQUENCE: 34

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
                20                  25                  30

Val Ala Val Val Ile Thr Ala Ala Asp Ser Arg Ser Gly Ile Leu
            35                  40                  45

Ala Leu Leu Lys Arg Thr Gly Phe His Leu Pro Val Phe Leu Tyr Ser
    50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
                100                 105                 110

Met Gly Asn Ser Thr Phe Ala Cys Pro Gly His Gln His Gly Ala Phe
            115                 120                 125

Phe Lys Lys His Pro Ala Gly Arg His Phe Tyr Asp Phe Phe Gly Glu
    130                 135                 140

Asn Val Phe Arg Ala Asp Met Cys Asn Ala Asp Val Lys Leu Gly Asp
145                 150                 155                 160

Leu Leu Ala His Glu Gly Ser Ala Lys Asp Ala Gln Lys Phe Ala Ala
                165                 170                 175

Lys Val Phe His Ala Asp Lys Thr Tyr Phe Val Leu Asn Gly Thr Ser
            180                 185                 190

Ala Ala Asn Lys Val Val Thr Asn Ala Leu Leu Thr Arg Gly Asp Leu
    195                 200                 205

Val Leu Phe Asp Arg Asn Asn His Lys Ser Asn His His Gly Ala Leu
210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270

Arg Pro Tyr Arg Leu Ala Ile Ile Gln Leu Gly Thr Tyr Asp Gly Thr
    275                 280                 285

Val Tyr Asn Ala Arg Gln Val Ile Asp Thr Val Gly His Leu Cys Asp
290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Gln Ala Gly Phe
            340                 345                 350

```
Ser Gln Thr Ser Gln Ile His Lys Lys Asp Asn His Ile Arg Gly Gln
                355                 360                 365

Ala Arg Phe Cys Pro His Lys Arg Leu Asn Asn Ala Phe Met Leu His
370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415

Val Glu Ile Gly Ile Glu Ala Arg Lys Ala Ile Leu Ala Arg Cys Lys
                420                 425                 430

Leu Phe Arg Pro Phe Ile Pro Pro Val Val Asp Gly Lys Leu Trp Gln
                435                 440                 445

Asp Tyr Pro Thr Ser Val Leu Ala Ser Asp Arg Arg Phe Phe Ser Phe
        450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                485                 490                 495

Ala Glu Thr Gly Glu Tyr Ser Asp Phe Gly Val Pro Ala Thr Ile Leu
                500                 505                 510

Ala His Tyr Leu Arg Glu Asn Gly Ile Val Pro Glu Lys Cys Asp Leu
        515                 520                 525

Asn Ser Ile Leu Phe Leu Thr Pro Ala Glu Ser His Glu Lys Leu
530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
        565                 570                 575

Val Arg Tyr Arg Asp Tyr Thr Leu Arg Gln Leu Cys Gln Glu Met His
                580                 585                 590

Asp Leu Tyr Val Ser Phe Asp Val Lys Asp Leu Gln Lys Ala Met Phe
        595                 600                 605

Arg Gln Gln Ser Phe Pro Ser Val Val Met Asn Pro Gln Asp Ala His
610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
                660                 665                 670

Phe Leu Ala Leu Glu Glu Gly Val Asn Leu Leu Pro Gly Phe Ser Pro
        675                 680                 685

Glu Leu Gln Gly Val Tyr Ser Glu Thr Asp Ala Asp Gly Val Lys Arg
690                 695                 700

Leu Tyr Gly Tyr Val Leu Lys
705                 710

<210> SEQ ID NO 35
<211> LENGTH: 711
<212> TYPE: PRT
<213> ORGANISM: Artificial Sequence
<220> FEATURE:
<223> OTHER INFORMATION: Modified ODC protein I163S

<400> SEQUENCE: 35
```

```
Met Lys Ser Met Asn Ile Ala Ala Ser Ser Glu Leu Val Ser Arg Leu
 1               5                  10                  15

Ser Ser His Arg Arg Val Val Ala Leu Gly Asp Thr Asp Phe Thr Asp
            20                  25                  30

Val Ala Ala Val Val Ile Thr Ala Ala Asp Ser Arg Ser Gly Ile Leu
            35                  40                  45

Ala Leu Leu Lys Arg Thr Gly Phe His Leu Pro Val Phe Leu Tyr Ser
 50                  55                  60

Glu His Ala Val Glu Leu Pro Ala Gly Val Thr Ala Val Ile Asn Gly
 65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
            115                 120                 125

Phe Lys Lys His Pro Ala Gly Arg His Phe Tyr Asp Phe Phe Gly Glu
            130                 135                 140

Asn Val Phe Arg Ala Asp Met Cys Asn Ala Asp Val Lys Leu Gly Asp
145                 150                 155                 160

Leu Leu Ser His Glu Gly Ser Ala Lys Asp Ala Gln Lys Phe Ala Ala
                165                 170                 175

Lys Val Phe His Ala Asp Lys Thr Tyr Phe Val Leu Asn Gly Thr Ser
                180                 185                 190

Ala Ala Asn Lys Val Val Thr Asn Ala Leu Leu Thr Arg Gly Asp Leu
                195                 200                 205

Val Leu Phe Asp Arg Asn Asn His Lys Ser Asn His His Gly Ala Leu
            210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270

Arg Pro Tyr Arg Leu Ala Ile Ile Gln Leu Gly Thr Tyr Asp Gly Thr
            275                 280                 285

Val Tyr Asn Ala Arg Gln Val Ile Asp Thr Val Gly His Leu Cys Asp
            290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Gln Ala Gly Phe
            340                 345                 350

Ser Gln Thr Ser Gln Ile His Lys Lys Asp Asn His Ile Arg Gly Gln
            355                 360                 365

Ala Arg Phe Cys Pro His Lys Arg Leu Asn Asn Ala Phe Met Leu His
            370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415

Val Glu Ile Gly Ile Glu Ala Arg Lys Ala Ile Leu Ala Arg Cys Lys
```

```
            420             425             430
Leu Phe Arg Pro Phe Ile Pro Pro Val Val Asp Gly Lys Leu Trp Gln
            435             440             445

Asp Tyr Pro Thr Ser Val Leu Ala Ser Asp Arg Arg Phe Phe Ser Phe
    450             455             460

Glu Pro Gly Ala Lys Trp His Gly Phe Glu Gly Tyr Ala Ala Asp Gln
465             470             475             480

Tyr Phe Val Asp Pro Cys Lys Leu Leu Leu Thr Thr Pro Gly Ile Asp
                485             490             495

Ala Glu Thr Gly Glu Tyr Ser Asp Phe Gly Val Pro Ala Thr Ile Leu
            500             505             510

Ala His Tyr Leu Arg Glu Asn Gly Ile Val Pro Glu Lys Cys Asp Leu
        515             520             525

Asn Ser Ile Leu Phe Leu Leu Thr Pro Ala Glu Ser His Glu Lys Leu
        530             535             540

Ala Gln Leu Val Ala Met Leu Ala Gln Phe Glu Gln His Ile Glu Asp
545             550             555             560

Asp Ser Pro Leu Val Glu Val Leu Pro Ser Val Tyr Asn Lys Tyr Pro
                565             570             575

Val Arg Tyr Arg Asp Tyr Thr Leu Arg Gln Leu Cys Gln Glu Met His
            580             585             590

Asp Leu Tyr Val Ser Phe Asp Val Lys Asp Leu Gln Lys Ala Met Phe
        595             600             605

Arg Gln Gln Ser Phe Pro Ser Val Val Met Asn Pro Gln Asp Ala His
    610             615             620

Ser Ala Tyr Ile Arg Gly Asp Val Glu Leu Val Arg Ile Arg Asp Ala
625             630             635             640

Glu Gly Arg Ile Ala Ala Glu Gly Ala Leu Pro Tyr Pro Pro Gly Val
                645             650             655

Leu Cys Val Val Pro Gly Glu Val Trp Gly Gly Ala Val Gln Arg Tyr
            660             665             670

Phe Leu Ala Leu Glu Glu Gly Val Asn Leu Leu Pro Gly Phe Ser Pro
        675             680             685

Glu Leu Gln Gly Val Tyr Ser Glu Thr Asp Ala Asp Gly Val Lys Arg
    690             695             700

Leu Tyr Gly Tyr Val Leu Lys
705             710

<210> SEQ ID NO 36
<211> LENGTH: 711
<212> TYPE: PRT
<213> ORGANISM: Artificial Sequence
<220> FEATURE:
<223> OTHER INFORMATION: Modified ODC protein I163G

<400> SEQUENCE: 36

Met Lys Ser Met Asn Ile Ala Ala Ser Ser Glu Leu Val Ser Arg Leu
1               5               10              15

Ser Ser His Arg Arg Val Val Ala Leu Gly Asp Thr Asp Phe Thr Asp
            20              25              30

Val Ala Ala Val Val Ile Thr Ala Asp Ser Arg Ser Gly Ile Leu
        35              40              45

Ala Leu Leu Lys Arg Thr Gly Phe His Leu Pro Val Phe Leu Tyr Ser
    50              55              60

Glu His Ala Val Glu Leu Pro Ala Gly Val Thr Ala Val Ile Asn Gly
```

-continued

```
            65                  70                  75                  80
Asn Glu Gln Gln Trp Leu Glu Leu Glu Ser Ala Ala Cys Gln Tyr Glu
                    85                  90                  95

Glu Asn Leu Leu Pro Pro Phe Tyr Asp Thr Leu Thr Gln Tyr Val Glu
                100                 105                 110

Met Gly Asn Ser Thr Phe Ala Cys Pro Gly His Gln His Gly Ala Phe
                115                 120                 125

Phe Lys Lys His Pro Ala Gly Arg His Phe Tyr Asp Phe Phe Gly Glu
            130                 135                 140

Asn Val Phe Arg Ala Asp Met Cys Asn Ala Asp Val Lys Leu Gly Asp
145                 150                 155                 160

Leu Leu Gly His Glu Gly Ser Ala Lys Asp Ala Gln Lys Phe Ala Ala
                165                 170                 175

Lys Val Phe His Ala Asp Lys Thr Tyr Phe Val Leu Asn Gly Thr Ser
                180                 185                 190

Ala Ala Asn Lys Val Val Thr Asn Ala Leu Leu Thr Arg Gly Asp Leu
                195                 200                 205

Val Leu Phe Asp Arg Asn Asn His Lys Ser Asn His His Gly Ala Leu
            210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
                260                 265                 270

Arg Pro Tyr Arg Leu Ala Ile Ile Gln Leu Gly Thr Tyr Asp Gly Thr
            275                 280                 285

Val Tyr Asn Ala Arg Gln Val Ile Asp Thr Val Gly His Leu Cys Asp
            290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Gln Ala Gly Phe
                340                 345                 350

Ser Gln Thr Ser Gln Ile His Lys Lys Asp Asn His Ile Arg Gly Gln
            355                 360                 365

Ala Arg Phe Cys Pro His Lys Arg Leu Asn Asn Ala Phe Met Leu His
            370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415

Val Glu Ile Gly Ile Glu Ala Arg Lys Ala Ile Leu Ala Arg Cys Lys
                420                 425                 430

Leu Phe Arg Pro Phe Ile Pro Pro Val Val Asp Gly Lys Leu Trp Gln
            435                 440                 445

Asp Tyr Pro Thr Ser Val Leu Ala Ser Asp Arg Arg Phe Phe Ser Phe
            450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                485                 490                 495
```

Ala Glu Thr Gly Glu Tyr Ser Asp Phe Gly Val Pro Ala Thr Ile Leu
            500                 505                 510

Ala His Tyr Leu Arg Glu Asn Gly Ile Val Pro Glu Lys Cys Asp Leu
            515                 520                 525

Asn Ser Ile Leu Phe Leu Leu Thr Pro Ala Glu Ser His Glu Lys Leu
        530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
            580                 585                 590

Asp Leu Tyr Val Ser Phe Asp Val Lys Asp Leu Gln Lys Ala Met Phe
        595                 600                 605

Arg Gln Gln Ser Phe Pro Ser Val Val Met Asn Pro Gln Asp Ala His
610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
            660                 665                 670

Phe Leu Ala Leu Glu Glu Gly Val Asn Leu Leu Pro Gly Phe Ser Pro
        675                 680                 685

Glu Leu Gln Gly Val Tyr Ser Glu Thr Asp Ala Asp Gly Val Lys Arg
690                 695                 700

Leu Tyr Gly Tyr Val Leu Lys
705                 710

<210> SEQ ID NO 37
<211> LENGTH: 711
<212> TYPE: PRT
<213> ORGANISM: Artificial Sequence
<220> FEATURE:
<223> OTHER INFORMATION: Modified ODC protein I163V

<400> SEQUENCE: 37

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
            20                  25                  30

Val Ala Ala Val Val Ile Thr Ala Ala Asp Ser Arg Ser Gly Ile Leu
        35                  40                  45

Ala Leu Leu Lys Arg Thr Gly Phe His Leu Pro Val Phe Leu Tyr Ser
    50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125

Phe Lys Lys His Pro Ala Gly Arg His Phe Tyr Asp Phe Phe Gly Glu
    130                 135                 140

```
Asn Val Phe Arg Ala Asp Met Cys Asn Ala Asp Val Lys Leu Gly Asp
145                 150                 155                 160

Leu Leu Val His Glu Gly Ser Ala Lys Asp Ala Gln Lys Phe Ala Ala
                165                 170                 175

Lys Val Phe His Ala Asp Lys Thr Tyr Phe Val Leu Asn Gly Thr Ser
                180                 185                 190

Ala Ala Asn Lys Val Val Thr Asn Ala Leu Leu Thr Arg Gly Asp Leu
                195                 200                 205

Val Leu Phe Asp Arg Asn Asn His Lys Ser Asn His His Gly Ala Leu
            210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
                260                 265                 270

Arg Pro Tyr Arg Leu Ala Ile Ile Gln Leu Gly Thr Tyr Asp Gly Thr
            275                 280                 285

Val Tyr Asn Ala Arg Gln Val Ile Asp Thr Val Gly His Leu Cys Asp
            290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Ala Gly Phe
                340                 345                 350

Ser Gln Thr Ser Gln Ile His Lys Lys Asp Asn His Ile Arg Gly Gln
            355                 360                 365

Ala Arg Phe Cys Pro His Lys Arg Leu Asn Asn Ala Phe Met Leu His
            370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415

Val Glu Ile Gly Ile Glu Ala Arg Lys Ala Ile Leu Ala Arg Cys Lys
                420                 425                 430

Leu Phe Arg Pro Phe Ile Pro Pro Val Val Asp Gly Lys Leu Trp Gln
            435                 440                 445

Asp Tyr Pro Thr Ser Val Leu Ala Ser Asp Arg Arg Phe Phe Ser Phe
            450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                485                 490                 495

Ala Glu Thr Gly Glu Tyr Ser Asp Phe Gly Val Pro Ala Thr Ile Leu
                500                 505                 510

Ala His Tyr Leu Arg Glu Asn Gly Ile Val Pro Glu Lys Cys Asp Leu
            515                 520                 525

Asn Ser Ile Leu Phe Leu Thr Pro Ala Glu Ser His Glu Lys Leu
            530                 535                 540

Ala Gln Leu Val Ala Met Leu Ala Gln Phe Glu Gln His Ile Glu Asp
545                 550                 555                 560
```

```
Asp Ser Pro Leu Val Glu Val Leu Pro Ser Val Tyr Asn Lys Tyr Pro
            565                 570                 575

Val Arg Tyr Arg Asp Tyr Thr Leu Arg Gln Leu Cys Gln Glu Met His
        580                 585                 590

Asp Leu Tyr Val Ser Phe Asp Val Lys Asp Leu Gln Lys Ala Met Phe
    595                 600                 605

Arg Gln Gln Ser Phe Pro Ser Val Val Met Asn Pro Gln Asp Ala His
610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
                660                 665                 670

Phe Leu Ala Leu Glu Glu Gly Val Asn Leu Leu Pro Gly Phe Ser Pro
            675                 680                 685

Glu Leu Gln Gly Val Tyr Ser Glu Thr Asp Ala Asp Gly Val Lys Arg
        690                 695                 700

Leu Tyr Gly Tyr Val Leu Lys
705                 710

<210> SEQ ID NO 38
<211> LENGTH: 711
<212> TYPE: PRT
<213> ORGANISM: Artificial Sequence
<220> FEATURE:
<223> OTHER INFORMATION: Modified ODC protein E165A

<400> SEQUENCE: 38

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
            20                  25                  30

Val Ala Ala Val Val Ile Thr Ala Ala Asp Ser Arg Ser Gly Ile Leu
        35                  40                  45

Ala Leu Leu Lys Arg Thr Gly Phe His Leu Pro Val Phe Leu Tyr Ser
    50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125

Phe Lys Lys His Pro Ala Gly Arg His Phe Tyr Asp Phe Phe Gly Glu
    130                 135                 140

Asn Val Phe Arg Ala Asp Met Cys Asn Ala Asp Val Lys Leu Gly Asp
145                 150                 155                 160

Leu Leu Ile His Ala Gly Ser Ala Lys Asp Ala Gln Lys Phe Ala Ala
                165                 170                 175

Lys Val Phe His Ala Asp Lys Thr Tyr Phe Val Leu Asn Gly Thr Ser
            180                 185                 190

Ala Ala Asn Lys Val Val Thr Asn Ala Leu Leu Thr Arg Gly Asp Leu
        195                 200                 205
```

```
Val Leu Phe Asp Arg Asn Asn His Lys Ser Asn His Gly Ala Leu
    210                 215                 220
Ile Gln Ala Gly Ala Thr Pro Val Tyr Leu Glu Ala Ser Arg Asn Pro
225                 230                 235                 240
Phe Gly Phe Ile Gly Gly Ile Asp Ala His Cys Phe Asn Glu Glu Tyr
                245                 250                 255
Leu Arg Gln Gln Ile Arg Asp Val Ala Pro Glu Lys Ala Asp Leu Pro
                260                 265                 270
Arg Pro Tyr Arg Leu Ala Ile Ile Gln Leu Gly Thr Tyr Asp Gly Thr
                275                 280                 285
Val Tyr Asn Ala Arg Gln Val Ile Asp Thr Val Gly His Leu Cys Asp
290                 295                 300
Tyr Ile Leu Phe Asp Ser Ala Trp Val Gly Tyr Gln Phe Ile Pro
305                 310                 315                 320
Met Met Ala Asp Ser Ser Pro Leu Leu Leu Glu Leu Asn Glu Asn Asp
                325                 330                 335
Pro Gly Ile Phe Val Thr Gln Ser Val His Lys Gln Ala Gly Phe
                340                 345                 350
Ser Gln Thr Ser Gln Ile His Lys Lys Asp Asn His Ile Arg Gly Gln
                355                 360                 365
Ala Arg Phe Cys Pro His Lys Arg Leu Asn Asn Ala Phe Met Leu His
                370                 375                 380
Ala Ser Thr Ser Pro Phe Tyr Pro Leu Phe Ala Ala Leu Asp Val Asn
385                 390                 395                 400
Ala Lys Ile His Glu Gly Glu Ser Gly Arg Arg Leu Trp Ala Glu Cys
                405                 410                 415
Val Glu Ile Gly Ile Glu Ala Arg Lys Ala Ile Leu Ala Arg Cys Lys
                420                 425                 430
Leu Phe Arg Pro Phe Ile Pro Pro Val Val Asp Gly Lys Leu Trp Gln
                435                 440                 445
Asp Tyr Pro Thr Ser Val Leu Ala Ser Asp Arg Arg Phe Phe Ser Phe
                450                 455                 460
Glu Pro Gly Ala Lys Trp His Gly Phe Glu Gly Tyr Ala Ala Asp Gln
465                 470                 475                 480
Tyr Phe Val Asp Pro Cys Lys Leu Leu Leu Thr Thr Pro Gly Ile Asp
                485                 490                 495
Ala Glu Thr Gly Glu Tyr Ser Asp Phe Gly Val Pro Ala Thr Ile Leu
                500                 505                 510
Ala His Tyr Leu Arg Glu Asn Gly Ile Val Pro Glu Lys Cys Asp Leu
                515                 520                 525
Asn Ser Ile Leu Phe Leu Leu Thr Pro Ala Glu Ser His Glu Lys Leu
530                 535                 540
Ala Gln Leu Val Ala Met Leu Ala Gln Phe Glu Gln His Ile Glu Asp
545                 550                 555                 560
Asp Ser Pro Leu Val Glu Val Leu Pro Ser Val Tyr Asn Lys Tyr Pro
                565                 570                 575
Val Arg Tyr Arg Asp Tyr Thr Leu Arg Gln Leu Cys Gln Glu Met His
                580                 585                 590
Asp Leu Tyr Val Ser Phe Asp Val Lys Asp Leu Gln Lys Ala Met Phe
                595                 600                 605
Arg Gln Gln Ser Phe Pro Ser Val Val Met Asn Pro Gln Asp Ala His
                610                 615                 620
Ser Ala Tyr Ile Arg Gly Asp Val Glu Leu Val Arg Ile Arg Asp Ala
```

```
                    625                 630                 635                 640
Glu Gly Arg Ile Ala Ala Glu Gly Ala Leu Pro Tyr Pro Pro Gly Val
                        645                 650                 655
Leu Cys Val Val Pro Gly Glu Val Trp Gly Gly Ala Val Gln Arg Tyr
                660                 665                 670
Phe Leu Ala Leu Glu Glu Gly Val Asn Leu Leu Pro Gly Phe Ser Pro
                675                 680                 685
Glu Leu Gln Gly Val Tyr Ser Glu Thr Asp Ala Asp Gly Val Lys Arg
                690                 695                 700
Leu Tyr Gly Tyr Val Leu Lys
705                 710

<210> SEQ ID NO 39
<211> LENGTH: 711
<212> TYPE: PRT
<213> ORGANISM: Artificial Sequence
<220> FEATURE:
<223> OTHER INFORMATION: Modified ODC protein E165S

<400> SEQUENCE: 39

Met Lys Ser Met Asn Ile Ala Ala Ser Ser Glu Leu Val Ser Arg Leu
1               5                   10                  15
Ser Ser His Arg Arg Val Val Ala Leu Gly Asp Thr Asp Phe Thr Asp
                20                  25                  30
Val Ala Ala Val Val Ile Thr Ala Ala Asp Ser Arg Ser Gly Ile Leu
                35                  40                  45
Ala Leu Leu Lys Arg Thr Gly Phe His Leu Pro Val Phe Leu Tyr Ser
50                  55                  60
Glu His Ala Val Glu Leu Pro Ala Gly Val Thr Ala Val Ile Asn Gly
65                  70                  75                  80
Asn Glu Gln Gln Trp Leu Glu Leu Glu Ser Ala Ala Cys Gln Tyr Glu
                85                  90                  95
Glu Asn Leu Leu Pro Pro Phe Tyr Asp Thr Leu Thr Gln Tyr Val Glu
                100                 105                 110
Met Gly Asn Ser Thr Phe Ala Cys Pro Gly His Gln His Gly Ala Phe
                115                 120                 125
Phe Lys Lys His Pro Ala Gly Arg His Phe Tyr Asp Phe Phe Gly Glu
                130                 135                 140
Asn Val Phe Arg Ala Asp Met Cys Asn Ala Asp Val Lys Leu Gly Asp
145                 150                 155                 160
Leu Leu Ile His Ser Gly Ser Ala Lys Asp Ala Gln Lys Phe Ala Ala
                165                 170                 175
Lys Val Phe His Ala Asp Lys Thr Tyr Phe Val Leu Asn Gly Thr Ser
                180                 185                 190
Ala Ala Asn Lys Val Val Thr Asn Ala Leu Leu Thr Arg Gly Asp Leu
                195                 200                 205
Val Leu Phe Asp Arg Asn Asn His Lys Ser Asn His His Gly Ala Leu
                210                 215                 220
Ile Gln Ala Gly Ala Thr Pro Val Tyr Leu Glu Ala Ser Arg Asn Pro
225                 230                 235                 240
Phe Gly Phe Ile Gly Gly Ile Asp Ala His Cys Phe Asn Glu Glu Tyr
                245                 250                 255
Leu Arg Gln Gln Ile Arg Asp Val Ala Pro Glu Lys Ala Asp Leu Pro
                260                 265                 270
Arg Pro Tyr Arg Leu Ala Ile Ile Gln Leu Gly Thr Tyr Asp Gly Thr
```

```
            275                 280                 285
Val Tyr Asn Ala Arg Gln Val Ile Asp Thr Val Gly His Leu Cys Asp
290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
            325                 330                 335

Pro Gly Ile Phe Val Thr Gln Ser Val His Lys Gln Gln Ala Gly Phe
        340                 345                 350

Ser Gln Thr Ser Gln Ile His Lys Lys Asp Asn His Ile Arg Gly Gln
            355                 360                 365

Ala Arg Phe Cys Pro His Lys Arg Leu Asn Asn Ala Phe Met Leu His
        370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415

Val Glu Ile Gly Ile Glu Ala Arg Lys Ala Ile Leu Ala Arg Cys Lys
            420                 425                 430

Leu Phe Arg Pro Phe Ile Pro Pro Val Val Asp Gly Lys Leu Trp Gln
        435                 440                 445

Asp Tyr Pro Thr Ser Val Leu Ala Ser Asp Arg Arg Phe Phe Ser Phe
450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                485                 490                 495

Ala Glu Thr Gly Glu Tyr Ser Asp Phe Gly Val Pro Ala Thr Ile Leu
            500                 505                 510

Ala His Tyr Leu Arg Glu Asn Gly Ile Val Pro Glu Lys Cys Asp Leu
        515                 520                 525

Asn Ser Ile Leu Phe Leu Leu Thr Pro Ala Glu Ser His Glu Lys Leu
530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
            580                 585                 590

Asp Leu Tyr Val Ser Phe Asp Val Lys Asp Leu Gln Lys Ala Met Phe
        595                 600                 605

Arg Gln Gln Ser Phe Pro Ser Val Val Met Asn Pro Gln Asp Ala His
610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
            660                 665                 670

Phe Leu Ala Leu Glu Glu Gly Val Asn Leu Leu Pro Gly Phe Ser Pro
        675                 680                 685

Glu Leu Gln Gly Val Tyr Ser Glu Thr Asp Ala Asp Gly Val Lys Arg
690                 695                 700
```

-continued

```
<210> SEQ ID NO 40
<211> LENGTH: 711
<212> TYPE: PRT
<213> ORGANISM: Artificial Sequence
<220> FEATURE:
<223> OTHER INFORMATION: Modified ODC protein E165G

<400> SEQUENCE: 40
```

```
Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
            20                  25                  30

Val Ala Ala Val Val Ile Thr Ala Ala Asp Ser Arg Ser Gly Ile Leu
        35                  40                  45

Ala Leu Leu Lys Arg Thr Gly Phe His Leu Pro Val Phe Leu Tyr Ser
    50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125

Phe Lys Lys His Pro Ala Gly Arg His Phe Tyr Asp Phe Phe Gly Glu
    130                 135                 140

Asn Val Phe Arg Ala Asp Met Cys Asn Ala Asp Val Lys Leu Gly Asp
145                 150                 155                 160

Leu Leu Ile His Gly Gly Ser Ala Lys Asp Ala Gln Lys Phe Ala Ala
                165                 170                 175

Lys Val Phe His Ala Asp Lys Thr Tyr Phe Val Leu Asn Gly Thr Ser
            180                 185                 190

Ala Ala Asn Lys Val Val Thr Asn Ala Leu Leu Thr Arg Gly Asp Leu
        195                 200                 205

Val Leu Phe Asp Arg Asn Asn His Lys Ser Asn His His Gly Ala Leu
    210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270

Arg Pro Tyr Arg Leu Ala Ile Ile Gln Leu Gly Thr Tyr Asp Gly Thr
        275                 280                 285

Val Tyr Asn Ala Arg Gln Val Ile Asp Thr Val Gly His Leu Cys Asp
    290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Gln Ala Gly Phe
            340                 345                 350
```

Ser Gln Thr Ser Gln Ile His Lys Lys Asp Asn His Ile Arg Gly Gln
            355                 360                 365

Ala Arg Phe Cys Pro His Lys Arg Leu Asn Asn Ala Phe Met Leu His
    370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415

Val Glu Ile Gly Ile Glu Ala Arg Lys Ala Ile Leu Ala Arg Cys Lys
            420                 425                 430

Leu Phe Arg Pro Phe Ile Pro Pro Val Val Asp Gly Lys Leu Trp Gln
        435                 440                 445

Asp Tyr Pro Thr Ser Val Leu Ala Ser Asp Arg Arg Phe Phe Ser Phe
    450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                485                 490                 495

Ala Glu Thr Gly Glu Tyr Ser Asp Phe Gly Val Pro Ala Thr Ile Leu
            500                 505                 510

Ala His Tyr Leu Arg Glu Asn Gly Ile Val Pro Glu Lys Cys Asp Leu
        515                 520                 525

Asn Ser Ile Leu Phe Leu Leu Thr Pro Ala Glu Ser His Glu Lys Leu
    530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
            580                 585                 590

Asp Leu Tyr Val Ser Phe Asp Val Lys Asp Leu Gln Lys Ala Met Phe
        595                 600                 605

Arg Gln Gln Ser Phe Pro Ser Val Val Met Asn Pro Gln Asp Ala His
    610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
            660                 665                 670

Phe Leu Ala Leu Glu Glu Gly Val Asn Leu Leu Pro Gly Phe Ser Pro
        675                 680                 685

Glu Leu Gln Gly Val Tyr Ser Glu Thr Asp Ala Asp Gly Val Lys Arg
    690                 695                 700

Leu Tyr Gly Tyr Val Leu Lys
705                 710

<210> SEQ ID NO 41
<211> LENGTH: 711
<212> TYPE: PRT
<213> ORGANISM: Artificial Sequence
<220> FEATURE:
<223> OTHER INFORMATION: Modified ODC protein E165V

<400> SEQUENCE: 41

-continued

```
Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
            20                  25                  30

Val Ala Ala Val Val Ile Thr Ala Ala Asp Ser Arg Ser Gly Ile Leu
            35                  40                  45

Ala Leu Leu Lys Arg Thr Gly Phe His Leu Pro Val Phe Leu Tyr Ser
        50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
            115                 120                 125

Phe Lys Lys His Pro Ala Gly Arg His Phe Tyr Asp Phe Phe Gly Glu
        130                 135                 140

Asn Val Phe Arg Ala Asp Met Cys Asn Ala Asp Val Lys Leu Gly Asp
145                 150                 155                 160

Leu Leu Ile His Val Gly Ser Ala Lys Asp Ala Gln Lys Phe Ala Ala
                165                 170                 175

Lys Val Phe His Ala Asp Lys Thr Tyr Phe Val Leu Asn Gly Thr Ser
            180                 185                 190

Ala Ala Asn Lys Val Val Thr Asn Ala Leu Leu Thr Arg Gly Asp Leu
        195                 200                 205

Val Leu Phe Asp Arg Asn Asn His Lys Ser Asn His His Gly Ala Leu
210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270

Arg Pro Tyr Arg Leu Ala Ile Ile Gln Leu Gly Thr Tyr Asp Gly Thr
        275                 280                 285

Val Tyr Asn Ala Arg Gln Val Ile Asp Thr Val Gly His Leu Cys Asp
    290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Gln Ala Gly Phe
            340                 345                 350

Ser Gln Thr Ser Gln Ile His Lys Lys Asp Asn His Ile Arg Gly Gln
        355                 360                 365

Ala Arg Phe Cys Pro His Lys Arg Leu Asn Asn Ala Phe Met Leu His
370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
            405                 410                 415
```

```
Val Glu Ile Gly Ile Glu Ala Arg Lys Ala Ile Leu Ala Arg Cys Lys
                420                 425                 430

Leu Phe Arg Pro Phe Ile Pro Pro Val Val Asp Gly Lys Leu Trp Gln
            435                 440                 445

Asp Tyr Pro Thr Ser Val Leu Ala Ser Asp Arg Arg Phe Phe Ser Phe
450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Thr Thr Pro Gly Ile Asp
                485                 490                 495

Ala Glu Thr Gly Glu Tyr Ser Asp Phe Gly Val Pro Ala Thr Ile Leu
                500                 505                 510

Ala His Tyr Leu Arg Glu Asn Gly Ile Val Pro Glu Lys Cys Asp Leu
            515                 520                 525

Asn Ser Ile Leu Phe Leu Leu Thr Pro Ala Glu Ser His Glu Lys Leu
530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
                580                 585                 590

Asp Leu Tyr Val Ser Phe Asp Val Lys Asp Leu Gln Lys Ala Met Phe
            595                 600                 605

Arg Gln Gln Ser Phe Pro Ser Val Val Met Asn Pro Gln Asp Ala His
610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
                660                 665                 670

Phe Leu Ala Leu Glu Glu Gly Val Asn Leu Leu Pro Gly Phe Ser Pro
            675                 680                 685

Glu Leu Gln Gly Val Tyr Ser Glu Thr Asp Ala Asp Gly Val Lys Arg
            690                 695                 700

Leu Tyr Gly Tyr Val Leu Lys
705                 710

<210> SEQ ID NO 42
<211> LENGTH: 711
<212> TYPE: PRT
<213> ORGANISM: Artificial Sequence
<220> FEATURE:
<223> OTHER INFORMATION: Modified ODC protein I163A E165A

<400> SEQUENCE: 42

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
            20                  25                  30

Val Ala Ala Val Val Ile Thr Ala Ala Asp Ser Arg Ser Gly Ile Leu
        35                  40                  45

Ala Leu Leu Lys Arg Thr Gly Phe His Leu Pro Val Phe Leu Tyr Ser
    50                  55                  60
```

-continued

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125

Phe Lys Lys His Pro Ala Gly Arg His Phe Tyr Asp Phe Phe Gly Glu
    130                 135                 140

Asn Val Phe Arg Ala Asp Met Cys Asn Ala Asp Val Lys Leu Gly Asp
145                 150                 155                 160

Leu Leu Ala His Ala Gly Ser Ala Lys Asp Ala Gln Lys Phe Ala Ala
                165                 170                 175

Lys Val Phe His Ala Asp Lys Thr Tyr Phe Val Leu Asn Gly Thr Ser
                180                 185                 190

Ala Ala Asn Lys Val Val Thr Asn Ala Leu Leu Thr Arg Gly Asp Leu
            195                 200                 205

Val Leu Phe Asp Arg Asn Asn His Lys Ser Asn His His Gly Ala Leu
210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270

Arg Pro Tyr Arg Leu Ala Ile Ile Gln Leu Gly Thr Tyr Asp Gly Thr
        275                 280                 285

Val Tyr Asn Ala Arg Gln Val Ile Asp Thr Val Gly His Leu Cys Asp
    290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Gln Ala Gly Phe
            340                 345                 350

Ser Gln Thr Ser Gln Ile His Lys Lys Asp Asn His Ile Arg Gly Gln
        355                 360                 365

Ala Arg Phe Cys Pro His Lys Arg Leu Asn Asn Ala Phe Met Leu His
    370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415

Val Glu Ile Gly Ile Glu Ala Arg Lys Ala Ile Leu Ala Arg Cys Lys
            420                 425                 430

Leu Phe Arg Pro Phe Ile Pro Pro Val Val Asp Gly Lys Leu Trp Gln
        435                 440                 445

Asp Tyr Pro Thr Ser Val Leu Ala Ser Asp Arg Arg Phe Phe Ser Phe
    450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp

```
            485                 490                 495
Ala Glu Thr Gly Glu Tyr Ser Asp Phe Gly Val Pro Ala Thr Ile Leu
            500                 505                 510

Ala His Tyr Leu Arg Glu Asn Gly Ile Val Pro Glu Lys Cys Asp Leu
            515                 520                 525

Asn Ser Ile Leu Phe Leu Thr Pro Ala Glu Ser His Glu Lys Leu
530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
            580                 585                 590

Asp Leu Tyr Val Ser Phe Asp Val Lys Asp Leu Gln Lys Ala Met Phe
            595                 600                 605

Arg Gln Gln Ser Phe Pro Ser Val Val Met Asn Pro Gln Asp Ala His
610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
            660                 665                 670

Phe Leu Ala Leu Glu Glu Gly Val Asn Leu Leu Pro Gly Phe Ser Pro
            675                 680                 685

Glu Leu Gln Gly Val Tyr Ser Glu Thr Asp Ala Asp Gly Val Lys Arg
690                 695                 700

Leu Tyr Gly Tyr Val Leu Lys
705                 710

<210> SEQ ID NO 43
<211> LENGTH: 711
<212> TYPE: PRT
<213> ORGANISM: Artificial Sequence
<220> FEATURE:
<223> OTHER INFORMATION: Modified ODC protein I163A E165S

<400> SEQUENCE: 43

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
                20                  25                  30

Val Ala Ala Val Val Ile Thr Ala Ala Asp Ser Arg Ser Gly Ile Leu
            35                  40                  45

Ala Leu Leu Lys Arg Thr Gly Phe His Leu Pro Val Phe Leu Tyr Ser
50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
            115                 120                 125

Phe Lys Lys His Pro Ala Gly Arg His Phe Tyr Asp Phe Phe Gly Glu
```

```
                130              135              140
Asn Val Phe Arg Ala Asp Met Cys Asn Ala Asp Val Lys Leu Gly Asp
145                 150              155              160

Leu Leu Ala His Ser Gly Ser Ala Lys Asp Ala Gln Lys Phe Ala Ala
                165              170              175

Lys Val Phe His Ala Asp Lys Thr Tyr Phe Val Leu Asn Gly Thr Ser
                180              185              190

Ala Ala Asn Lys Val Val Thr Asn Ala Leu Leu Thr Arg Gly Asp Leu
                195              200              205

Val Leu Phe Asp Arg Asn Asn His Lys Ser Asn His His Gly Ala Leu
                210              215              220

Ile Gln Ala Gly Ala Thr Pro Val Tyr Leu Glu Ala Ser Arg Asn Pro
225                 230              235              240

Phe Gly Phe Ile Gly Gly Ile Asp Ala His Cys Phe Asn Glu Glu Tyr
                245              250              255

Leu Arg Gln Gln Ile Arg Asp Val Ala Pro Glu Lys Ala Asp Leu Pro
                260              265              270

Arg Pro Tyr Arg Leu Ala Ile Ile Gln Leu Gly Thr Tyr Asp Gly Thr
                275              280              285

Val Tyr Asn Ala Arg Gln Val Ile Asp Thr Val Gly His Leu Cys Asp
                290              295              300

Tyr Ile Leu Phe Asp Ser Ala Trp Val Gly Tyr Glu Gln Phe Ile Pro
305                 310              315              320

Met Met Ala Asp Ser Ser Pro Leu Leu Leu Glu Leu Asn Glu Asn Asp
                325              330              335

Pro Gly Ile Phe Val Thr Gln Ser Val His Lys Gln Gln Ala Gly Phe
                340              345              350

Ser Gln Thr Ser Gln Ile His Lys Lys Asp Asn His Ile Arg Gly Gln
                355              360              365

Ala Arg Phe Cys Pro His Lys Arg Leu Asn Asn Ala Phe Met Leu His
                370              375              380

Ala Ser Thr Ser Pro Phe Tyr Pro Leu Phe Ala Ala Leu Asp Val Asn
385                 390              395              400

Ala Lys Ile His Glu Gly Glu Ser Gly Arg Arg Leu Trp Ala Glu Cys
                405              410              415

Val Glu Ile Gly Ile Glu Ala Arg Lys Ala Ile Leu Ala Arg Cys Lys
                420              425              430

Leu Phe Arg Pro Phe Ile Pro Pro Val Val Asp Gly Lys Leu Trp Gln
                435              440              445

Asp Tyr Pro Thr Ser Val Leu Ala Ser Asp Arg Arg Phe Phe Ser Phe
                450              455              460

Glu Pro Gly Ala Lys Trp His Gly Phe Glu Gly Tyr Ala Ala Asp Gln
465                 470              475              480

Tyr Phe Val Asp Pro Cys Lys Leu Leu Leu Thr Thr Pro Gly Ile Asp
                485              490              495

Ala Glu Thr Gly Glu Tyr Ser Asp Phe Gly Val Pro Ala Thr Ile Leu
                500              505              510

Ala His Tyr Leu Arg Glu Asn Gly Ile Val Pro Glu Lys Cys Asp Leu
                515              520              525

Asn Ser Ile Leu Phe Leu Thr Pro Ala Glu Ser His Glu Lys Leu
                530              535              540

Ala Gln Leu Val Ala Met Leu Ala Gln Phe Glu Gln His Ile Glu Asp
545                 550              555              560
```

```
Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
            580                 585                 590

Asp Leu Tyr Val Ser Phe Asp Val Lys Asp Leu Gln Lys Ala Met Phe
        595                 600                 605

Arg Gln Gln Ser Phe Pro Ser Val Val Met Asn Pro Gln Asp Ala His
    610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
                660                 665                 670

Phe Leu Ala Leu Glu Glu Gly Val Asn Leu Leu Pro Gly Phe Ser Pro
            675                 680                 685

Glu Leu Gln Gly Val Tyr Ser Glu Thr Asp Ala Asp Gly Val Lys Arg
        690                 695                 700

Leu Tyr Gly Tyr Val Leu Lys
705                 710

<210> SEQ ID NO 44
<211> LENGTH: 711
<212> TYPE: PRT
<213> ORGANISM: Artificial Sequence
<220> FEATURE:
<223> OTHER INFORMATION: Modified ODC protein I163A E165G

<400> SEQUENCE: 44

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
                20                  25                  30

Val Ala Ala Val Val Ile Thr Ala Ala Asp Ser Arg Ser Gly Ile Leu
            35                  40                  45

Ala Leu Leu Lys Arg Thr Gly Phe His Leu Pro Val Phe Leu Tyr Ser
        50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125

Phe Lys Lys His Pro Ala Gly Arg His Phe Tyr Asp Phe Phe Gly Glu
    130                 135                 140

Asn Val Phe Arg Ala Asp Met Cys Asn Ala Asp Val Lys Leu Gly Asp
145                 150                 155                 160

Leu Leu Ala His Gly Gly Ser Lys Asp Ala Gln Lys Phe Ala Ala
                165                 170                 175

Lys Val Phe His Ala Asp Lys Thr Tyr Phe Val Leu Asn Gly Thr Ser
            180                 185                 190

Ala Ala Asn Lys Val Val Thr Asn Ala Leu Leu Thr Arg Gly Asp Leu
        195                 200                 205
```

```
Val Leu Phe Asp Arg Asn Asn His Lys Ser Asn His His Gly Ala Leu
    210                 215                 220
Ile Gln Ala Gly Ala Thr Pro Val Tyr Leu Glu Ala Ser Arg Asn Pro
225                 230                 235                 240
Phe Gly Phe Ile Gly Gly Ile Asp Ala His Cys Phe Asn Glu Glu Tyr
                245                 250                 255
Leu Arg Gln Gln Ile Arg Asp Val Ala Pro Glu Lys Ala Asp Leu Pro
                260                 265                 270
Arg Pro Tyr Arg Leu Ala Ile Ile Gln Leu Gly Thr Tyr Asp Gly Thr
                275                 280                 285
Val Tyr Asn Ala Arg Gln Val Ile Asp Thr Val Gly His Leu Cys Asp
    290                 295                 300
Tyr Ile Leu Phe Asp Ser Ala Trp Val Gly Tyr Glu Gln Phe Ile Pro
305                 310                 315                 320
Met Met Ala Asp Ser Ser Pro Leu Leu Leu Glu Leu Asn Glu Asn Asp
                325                 330                 335
Pro Gly Ile Phe Val Thr Gln Ser Val His Lys Gln Ala Gly Phe
                340                 345                 350
Ser Gln Thr Ser Gln Ile His Lys Lys Asp Asn His Ile Arg Gly Gln
                355                 360                 365
Ala Arg Phe Cys Pro His Lys Arg Leu Asn Asn Ala Phe Met Leu His
    370                 375                 380
Ala Ser Thr Ser Pro Phe Tyr Pro Leu Phe Ala Ala Leu Asp Val Asn
385                 390                 395                 400
Ala Lys Ile His Glu Gly Glu Ser Gly Arg Arg Leu Trp Ala Glu Cys
                405                 410                 415
Val Glu Ile Gly Ile Glu Ala Arg Lys Ala Ile Leu Ala Arg Cys Lys
                420                 425                 430
Leu Phe Arg Pro Phe Ile Pro Pro Val Val Asp Gly Lys Leu Trp Gln
    435                 440                 445
Asp Tyr Pro Thr Ser Val Leu Ala Ser Asp Arg Arg Phe Phe Ser Phe
450                 455                 460
Glu Pro Gly Ala Lys Trp His Gly Phe Glu Gly Tyr Ala Ala Asp Gln
465                 470                 475                 480
Tyr Phe Val Asp Pro Cys Lys Leu Leu Leu Thr Thr Pro Gly Ile Asp
                485                 490                 495
Ala Glu Thr Gly Glu Tyr Ser Asp Phe Gly Val Pro Ala Thr Ile Leu
                500                 505                 510
Ala His Tyr Leu Arg Glu Asn Gly Ile Val Pro Glu Lys Cys Asp Leu
    515                 520                 525
Asn Ser Ile Leu Phe Leu Leu Thr Pro Ala Glu Ser His Glu Lys Leu
530                 535                 540
Ala Gln Leu Val Ala Met Leu Ala Gln Phe Glu Gln His Ile Glu Asp
545                 550                 555                 560
Asp Ser Pro Leu Val Glu Val Leu Pro Ser Val Tyr Asn Lys Tyr Pro
                565                 570                 575
Val Arg Tyr Arg Asp Tyr Thr Leu Arg Gln Leu Cys Gln Glu Met His
                580                 585                 590
Asp Leu Tyr Val Ser Phe Asp Val Lys Asp Leu Gln Lys Ala Met Phe
    595                 600                 605
Arg Gln Gln Ser Phe Pro Ser Val Val Met Asn Pro Gln Asp Ala His
610                 615                 620
```

```
Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
            645                 650                 655

Leu Cys Val Val Pro Gly Glu Val Trp Gly Gly Ala Val Gln Arg Tyr
            660                 665                 670

Phe Leu Ala Leu Glu Glu Gly Val Asn Leu Leu Pro Gly Phe Ser Pro
        675                 680                 685

Glu Leu Gln Gly Val Tyr Ser Glu Thr Asp Ala Asp Gly Val Lys Arg
        690                 695                 700

Leu Tyr Gly Tyr Val Leu Lys
705                 710
```

<210> SEQ ID NO 45
<211> LENGTH: 711
<212> TYPE: PRT
<213> ORGANISM: Artificial Sequence
<220> FEATURE:
<223> OTHER INFORMATION: Modified ODC protein I163A E165V

<400> SEQUENCE: 45

```
Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
            20                  25                  30

Val Ala Ala Val Val Ile Thr Ala Ala Asp Ser Arg Ser Gly Ile Leu
        35                  40                  45

Ala Leu Leu Lys Arg Thr Gly Phe His Leu Pro Val Phe Leu Tyr Ser
    50                  55                  60

Glu His Ala Val Glu Leu Pro Ala Gly Val Thr Ala Val Ile Asn Gly
65                  70                  75                  80

Asn Glu Gln Gln Trp Leu Glu Leu Gly Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125

Phe Lys Lys His Pro Ala Gly Arg His Phe Tyr Asp Phe Phe Gly Glu
    130                 135                 140

Asn Val Phe Arg Ala Asp Met Cys Asn Ala Asp Val Lys Leu Gly Asp
145                 150                 155                 160

Leu Leu Ala His Val Gly Ser Ala Lys Asp Ala Gln Lys Phe Ala Ala
                165                 170                 175

Lys Val Phe His Ala Asp Lys Thr Tyr Phe Val Leu Asn Gly Thr Ser
            180                 185                 190

Ala Ala Asn Lys Val Val Thr Asn Ala Leu Leu Thr Arg Gly Asp Leu
        195                 200                 205

Val Leu Phe Asp Arg Asn Asn His Lys Ser Asn His His Gly Ala Leu
    210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270
```

```
Arg Pro Tyr Arg Leu Ala Ile Ile Gln Leu Gly Thr Tyr Asp Gly Thr
            275                 280                 285

Val Tyr Asn Ala Arg Gln Val Ile Asp Thr Val Gly His Leu Cys Asp
        290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Gln Ala Gly Phe
                340                 345                 350

Ser Gln Thr Ser Gln Ile His Lys Lys Asp Asn His Ile Arg Gly Gln
            355                 360                 365

Ala Arg Phe Cys Pro His Lys Arg Leu Asn Asn Ala Phe Met Leu His
        370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415

Val Glu Ile Gly Ile Glu Ala Arg Lys Ala Ile Leu Ala Arg Cys Lys
                420                 425                 430

Leu Phe Arg Pro Phe Ile Pro Pro Val Val Asp Gly Lys Leu Trp Gln
        435                 440                 445

Asp Tyr Pro Thr Ser Val Leu Ala Ser Asp Arg Arg Phe Phe Ser Phe
        450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                485                 490                 495

Ala Glu Thr Gly Glu Tyr Ser Asp Phe Gly Val Pro Ala Thr Ile Leu
                500                 505                 510

Ala His Tyr Leu Arg Glu Asn Gly Ile Val Pro Glu Lys Cys Asp Leu
            515                 520                 525

Asn Ser Ile Leu Phe Leu Leu Thr Pro Ala Glu Ser His Glu Lys Leu
530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
        580                 585                 590

Asp Leu Tyr Val Ser Phe Asp Val Lys Asp Leu Gln Lys Ala Met Phe
        595                 600                 605

Arg Gln Gln Ser Phe Pro Ser Val Val Met Asn Pro Gln Asp Ala His
        610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
                660                 665                 670

Phe Leu Ala Leu Glu Glu Gly Val Asn Leu Leu Pro Gly Phe Ser Pro
        675                 680                 685

Glu Leu Gln Gly Val Tyr Ser Glu Thr Asp Ala Asp Gly Val Lys Arg
```

```
                690                 695                 700
Leu Tyr Gly Tyr Val Leu Lys
705                 710

<210> SEQ ID NO 46
<211> LENGTH: 711
<212> TYPE: PRT
<213> ORGANISM: Artificial Sequence
<220> FEATURE:
<223> OTHER INFORMATION: Modified ODC protein I163S E165A

<400> SEQUENCE: 46

Met Lys Ser Met Asn Ile Ala Ala Ser Glu Leu Val Ser Arg Leu
1               5                   10                  15

Ser Ser His Arg Arg Val Val Ala Leu Gly Asp Thr Asp Phe Thr Asp
                20                  25                  30

Val Ala Ala Val Ile Thr Ala Ala Asp Ser Arg Ser Gly Ile Leu
            35                  40                  45

Ala Leu Leu Lys Arg Thr Gly Phe His Leu Pro Val Phe Leu Tyr Ser
        50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125

Phe Lys Lys His Pro Ala Gly Arg His Phe Tyr Asp Phe Phe Gly Glu
    130                 135                 140

Asn Val Phe Arg Ala Asp Met Cys Asn Ala Asp Val Lys Leu Gly Asp
145                 150                 155                 160

Leu Leu Ser His Ala Gly Ser Ala Lys Asp Ala Gln Lys Phe Ala Ala
                165                 170                 175

Lys Val Phe His Ala Asp Lys Thr Tyr Phe Val Leu Asn Gly Thr Ser
            180                 185                 190

Ala Ala Asn Lys Val Val Thr Asn Ala Leu Leu Thr Arg Gly Asp Leu
        195                 200                 205

Val Leu Phe Asp Arg Asn Asn His Lys Ser Asn His His Gly Ala Leu
    210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270

Arg Pro Tyr Arg Leu Ala Ile Ile Gln Leu Gly Thr Tyr Asp Gly Thr
        275                 280                 285

Val Tyr Asn Ala Arg Gln Val Ile Asp Thr Val Gly His Leu Cys Asp
    290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Gln Ala Gly Phe
```

```
                    340                 345                 350
Ser Gln Thr Ser Gln Ile His Lys Lys Asp Asn His Ile Arg Gly Gln
                355                 360                 365

Ala Arg Phe Cys Pro His Lys Arg Leu Asn Asn Ala Phe Met Leu His
            370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415

Val Glu Ile Gly Ile Glu Ala Arg Lys Ala Ile Leu Ala Arg Cys Lys
            420                 425                 430

Leu Phe Arg Pro Phe Ile Pro Pro Val Val Asp Gly Lys Leu Trp Gln
            435                 440                 445

Asp Tyr Pro Thr Ser Val Leu Ala Ser Asp Arg Arg Phe Phe Ser Phe
        450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                485                 490                 495

Ala Glu Thr Gly Glu Tyr Ser Asp Phe Gly Val Pro Ala Thr Ile Leu
            500                 505                 510

Ala His Tyr Leu Arg Glu Asn Gly Ile Val Pro Glu Lys Cys Asp Leu
        515                 520                 525

Asn Ser Ile Leu Phe Leu Leu Thr Pro Ala Glu Ser His Glu Lys Leu
    530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
            580                 585                 590

Asp Leu Tyr Val Ser Phe Asp Val Lys Asp Leu Gln Lys Ala Met Phe
        595                 600                 605

Arg Gln Gln Ser Phe Pro Ser Val Val Met Asn Pro Gln Asp Ala His
    610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
            660                 665                 670

Phe Leu Ala Leu Glu Glu Gly Val Asn Leu Leu Pro Gly Phe Ser Pro
        675                 680                 685

Glu Leu Gln Gly Val Tyr Ser Glu Thr Asp Ala Asp Gly Val Lys Arg
    690                 695                 700

Leu Tyr Gly Tyr Val Leu Lys
705                 710

<210> SEQ ID NO 47
<211> LENGTH: 711
<212> TYPE: PRT
<213> ORGANISM: Artificial Sequence
<220> FEATURE:
<223> OTHER INFORMATION: Modified ODC protein I163S E165S
```

```
<400> SEQUENCE: 47

Met Lys Ser Met Asn Ile Ala Ala Ser Ser Glu Leu Val Ser Arg Leu
 1               5                  10                  15

Ser Ser His Arg Arg Val Val Ala Leu Gly Asp Thr Asp Phe Thr Asp
            20                  25                  30

Val Ala Ala Val Val Ile Thr Ala Ala Asp Ser Arg Ser Gly Ile Leu
        35                  40                  45

Ala Leu Leu Lys Arg Thr Gly Phe His Leu Pro Val Phe Leu Tyr Ser
    50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125

Phe Lys Lys His Pro Ala Gly Arg His Phe Tyr Asp Phe Phe Gly Glu
    130                 135                 140

Asn Val Phe Arg Ala Asp Met Cys Asn Ala Asp Val Lys Leu Gly Asp
145                 150                 155                 160

Leu Leu Ser His Ser Gly Ser Ala Lys Asp Ala Gln Lys Phe Ala Ala
                165                 170                 175

Lys Val Phe His Ala Asp Lys Thr Tyr Phe Val Leu Asn Gly Thr Ser
            180                 185                 190

Ala Ala Asn Lys Val Val Thr Asn Ala Leu Leu Thr Arg Gly Asp Leu
        195                 200                 205

Val Leu Phe Asp Arg Asn Asn His Lys Ser Asn His His Gly Ala Leu
    210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270

Arg Pro Tyr Arg Leu Ala Ile Ile Gln Leu Gly Thr Tyr Asp Gly Thr
        275                 280                 285

Val Tyr Asn Ala Arg Gln Val Ile Asp Thr Val Gly His Leu Cys Asp
    290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Gln Ala Gly Phe
            340                 345                 350

Ser Gln Thr Ser Gln Ile His Lys Lys Asp Asn His Ile Arg Gly Gln
        355                 360                 365

Ala Arg Phe Cys Pro His Lys Arg Leu Asn Asn Ala Phe Met Leu His
    370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415
```

Val Glu Ile Gly Ile Glu Ala Arg Lys Ala Ile Leu Ala Arg Cys Lys
            420                 425                 430

Leu Phe Arg Pro Phe Ile Pro Pro Val Val Asp Gly Lys Leu Trp Gln
            435                 440                 445

Asp Tyr Pro Thr Ser Val Leu Ala Ser Asp Arg Arg Phe Phe Ser Phe
            450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
            485                 490                 495

Ala Glu Thr Gly Glu Tyr Ser Asp Phe Gly Val Pro Ala Thr Ile Leu
            500                 505                 510

Ala His Tyr Leu Arg Glu Asn Gly Ile Val Pro Glu Lys Cys Asp Leu
            515                 520                 525

Asn Ser Ile Leu Phe Leu Leu Thr Pro Ala Glu Ser His Glu Lys Leu
530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
            565                 570                 575

Val Arg Tyr Arg Asp Tyr Thr Leu Arg Gln Leu Cys Gln Glu Met His
            580                 585                 590

Asp Leu Tyr Val Ser Phe Asp Val Lys Asp Leu Gln Lys Ala Met Phe
            595                 600                 605

Arg Gln Gln Ser Phe Pro Ser Val Val Met Asn Pro Gln Asp Ala His
            610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
            645                 650                 655

Leu Cys Val Val Pro Gly Glu Val Trp Gly Gly Ala Val Gln Arg Tyr
            660                 665                 670

Phe Leu Ala Leu Glu Glu Gly Val Asn Leu Leu Pro Gly Phe Ser Pro
            675                 680                 685

Glu Leu Gln Gly Val Tyr Ser Glu Thr Asp Ala Asp Gly Val Lys Arg
            690                 695                 700

Leu Tyr Gly Tyr Val Leu Lys
705                 710

<210> SEQ ID NO 48
<211> LENGTH: 711
<212> TYPE: PRT
<213> ORGANISM: Artificial Sequence
<220> FEATURE:
<223> OTHER INFORMATION: Modified ODC protein I163S E165G

<400> SEQUENCE: 48

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
            20                  25                  30

Val Ala Ala Val Val Ile Thr Ala Ala Asp Ser Arg Ser Gly Ile Leu
            35                  40                  45

Ala Leu Leu Lys Arg Thr Gly Phe His Leu Pro Val Phe Leu Tyr Ser
        50                  55                  60

```
Glu His Ala Val Glu Leu Pro Ala Gly Val Thr Ala Val Ile Asn Gly
 65                  70                  75                  80

Asn Glu Gln Gln Trp Leu Glu Leu Glu Ser Ala Ala Cys Gln Tyr Glu
                 85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
            115                 120                 125

Phe Lys Lys His Pro Ala Gly Arg His Phe Tyr Asp Phe Phe Gly Glu
            130                 135                 140

Asn Val Phe Arg Ala Asp Met Cys Asn Ala Asp Val Lys Leu Gly Asp
145                 150                 155                 160

Leu Leu Ser His Gly Gly Ser Ala Lys Asp Ala Gln Lys Phe Ala Ala
                165                 170                 175

Lys Val Phe His Ala Asp Lys Thr Tyr Phe Val Leu Asn Gly Thr Ser
                180                 185                 190

Ala Ala Asn Lys Val Val Thr Asn Ala Leu Leu Thr Arg Gly Asp Leu
            195                 200                 205

Val Leu Phe Asp Arg Asn Asn His Lys Ser Asn His His Gly Ala Leu
210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270

Arg Pro Tyr Arg Leu Ala Ile Ile Gln Leu Gly Thr Tyr Asp Gly Thr
            275                 280                 285

Val Tyr Asn Ala Arg Gln Val Ile Asp Thr Val Gly His Leu Cys Asp
290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Gln Ala Gly Phe
            340                 345                 350

Ser Gln Thr Ser Gln Ile His Lys Lys Asp Asn His Ile Arg Gly Gln
            355                 360                 365

Ala Arg Phe Cys Pro His Lys Arg Leu Asn Asn Ala Phe Met Leu His
            370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415

Val Glu Ile Gly Ile Glu Ala Arg Lys Ala Ile Leu Ala Arg Cys Lys
                420                 425                 430

Leu Phe Arg Pro Phe Ile Pro Pro Val Val Asp Gly Lys Leu Trp Gln
            435                 440                 445

Asp Tyr Pro Thr Ser Val Leu Ala Ser Asp Arg Arg Phe Phe Ser Phe
            450                 455                 460

Glu Pro Gly Ala Lys Trp His Gly Phe Glu Gly Tyr Ala Ala Asp Gln
465                 470                 475                 480
```

-continued

```
Tyr Phe Val Asp Pro Cys Lys Leu Leu Leu Thr Thr Pro Gly Ile Asp
            485                 490                 495

Ala Glu Thr Gly Glu Tyr Ser Asp Phe Gly Val Pro Ala Thr Ile Leu
        500                 505                 510

Ala His Tyr Leu Arg Glu Asn Gly Ile Val Pro Glu Lys Cys Asp Leu
    515                 520                 525

Asn Ser Ile Leu Phe Leu Thr Pro Ala Glu Ser His Glu Lys Leu
530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
            580                 585                 590

Asp Leu Tyr Val Ser Phe Asp Val Lys Asp Leu Gln Lys Ala Met Phe
        595                 600                 605

Arg Gln Gln Ser Phe Pro Ser Val Val Met Asn Pro Gly Asp Ala His
    610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Ala Val Gln Arg Tyr
            660                 665                 670

Phe Leu Ala Leu Glu Gly Val Asn Leu Leu Pro Gly Phe Ser Pro
        675                 680                 685

Glu Leu Gln Gly Val Tyr Ser Glu Thr Asp Ala Asp Gly Val Lys Arg
    690                 695                 700

Leu Tyr Gly Tyr Val Leu Lys
705                 710

<210> SEQ ID NO 49
<211> LENGTH: 711
<212> TYPE: PRT
<213> ORGANISM: Artificial Sequence
<220> FEATURE:
<223> OTHER INFORMATION: Modified ODC protein I163S E165V

<400> SEQUENCE: 49

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
            20                  25                  30

Val Ala Ala Val Val Ile Thr Ala Ala Asp Ser Arg Ser Gly Ile Leu
        35                  40                  45

Ala Leu Leu Lys Arg Thr Gly Phe His Leu Pro Val Phe Leu Tyr Ser
    50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125
```

-continued

```
Phe Lys Lys His Pro Ala Gly Arg His Phe Tyr Asp Phe Phe Gly Glu
    130                 135                 140
Asn Val Phe Arg Ala Asp Met Cys Asn Ala Asp Val Lys Leu Gly Asp
145                 150                 155                 160
Leu Leu Ser His Val Gly Ser Ala Lys Asp Ala Gln Lys Phe Ala Ala
                165                 170                 175
Lys Val Phe His Ala Asp Lys Thr Tyr Phe Val Leu Asn Gly Thr Ser
                180                 185                 190
Ala Ala Asn Lys Val Val Thr Asn Ala Leu Leu Thr Arg Gly Asp Leu
            195                 200                 205
Val Leu Phe Asp Arg Asn Asn His Lys Ser Asn His His Gly Ala Leu
    210                 215                 220
Ile Gln Ala Gly Ala Thr Pro Val Tyr Leu Glu Ala Ser Arg Asn Pro
225                 230                 235                 240
Phe Gly Phe Ile Gly Gly Ile Asp Ala His Cys Phe Asn Glu Glu Tyr
                245                 250                 255
Leu Arg Gln Gln Ile Arg Asp Val Ala Pro Glu Lys Ala Asp Leu Pro
            260                 265                 270
Arg Pro Tyr Arg Leu Ala Ile Ile Gln Leu Gly Thr Tyr Asp Gly Thr
    275                 280                 285
Val Tyr Asn Ala Arg Gln Val Ile Asp Thr Val Gly His Leu Cys Asp
    290                 295                 300
Tyr Ile Leu Phe Asp Ser Ala Trp Val Gly Tyr Glu Gln Phe Ile Pro
305                 310                 315                 320
Met Met Ala Asp Ser Ser Pro Leu Leu Leu Glu Leu Asn Glu Asn Asp
                325                 330                 335
Pro Gly Ile Phe Val Thr Gln Ser Val His Lys Gln Gln Ala Gly Phe
            340                 345                 350
Ser Gln Thr Ser Gln Ile His Lys Lys Asp Asn His Ile Arg Gly Gln
    355                 360                 365
Ala Arg Phe Cys Pro His Lys Arg Leu Asn Asn Ala Phe Met Leu His
    370                 375                 380
Ala Ser Thr Ser Pro Phe Tyr Pro Leu Phe Ala Ala Leu Asp Val Asn
385                 390                 395                 400
Ala Lys Ile His Glu Gly Glu Ser Gly Arg Arg Leu Trp Ala Glu Cys
                405                 410                 415
Val Glu Ile Gly Ile Glu Ala Arg Lys Ala Ile Leu Ala Arg Cys Lys
            420                 425                 430
Leu Phe Arg Pro Phe Ile Pro Pro Val Val Asp Gly Lys Leu Trp Gln
    435                 440                 445
Asp Tyr Pro Thr Ser Val Leu Ala Ser Asp Arg Arg Phe Phe Ser Phe
450                 455                 460
Glu Pro Gly Ala Lys Trp His Gly Phe Glu Gly Tyr Ala Ala Asp Gln
465                 470                 475                 480
Tyr Phe Val Asp Pro Cys Lys Leu Leu Leu Thr Thr Pro Gly Ile Asp
                485                 490                 495
Ala Glu Thr Gly Glu Tyr Ser Asp Phe Gly Val Pro Ala Thr Ile Leu
            500                 505                 510
Ala His Tyr Leu Arg Glu Asn Gly Ile Val Pro Glu Lys Cys Asp Leu
    515                 520                 525
Asn Ser Ile Leu Phe Leu Thr Pro Ala Glu Ser His Glu Lys Leu
530                 535                 540
Ala Gln Leu Val Ala Met Leu Ala Gln Phe Glu Gln His Ile Glu Asp
```

```
                545                 550                 555                 560
Asp Ser Pro Leu Val Glu Val Leu Pro Ser Val Tyr Asn Lys Tyr Pro
                    565                 570                 575
Val Arg Tyr Arg Asp Tyr Thr Leu Arg Gln Leu Cys Gln Glu Met His
                    580                 585                 590
Asp Leu Tyr Val Ser Phe Asp Val Lys Asp Leu Gln Lys Ala Met Phe
                    595                 600                 605
Arg Gln Gln Ser Phe Pro Ser Val Val Met Asn Pro Gln Asp Ala His
                    610                 615                 620
Ser Ala Tyr Ile Arg Gly Asp Val Glu Leu Val Arg Ile Arg Asp Ala
625                 630                 635                 640
Glu Gly Arg Ile Ala Ala Glu Gly Ala Leu Pro Tyr Pro Pro Gly Val
                    645                 650                 655
Leu Cys Val Val Pro Gly Glu Val Trp Gly Gly Ala Val Gln Arg Tyr
                    660                 665                 670
Phe Leu Ala Leu Glu Glu Gly Val Asn Leu Leu Pro Gly Phe Ser Pro
                    675                 680                 685
Glu Leu Gln Gly Val Tyr Ser Glu Thr Asp Ala Asp Gly Val Lys Arg
                    690                 695                 700
Leu Tyr Gly Tyr Val Leu Lys
705                 710

<210> SEQ ID NO 50
<211> LENGTH: 711
<212> TYPE: PRT
<213> ORGANISM: Artificial Sequence
<220> FEATURE:
<223> OTHER INFORMATION: Modified ODC protein I163G E165A

<400> SEQUENCE: 50

Met Lys Ser Met Asn Ile Ala Ala Ser Ser Glu Leu Val Ser Arg Leu
1               5                   10                  15
Ser Ser His Arg Arg Val Val Ala Leu Gly Asp Thr Asp Phe Thr Asp
                20                  25                  30
Val Ala Ala Val Val Ile Thr Ala Ala Asp Ser Arg Ser Gly Ile Leu
                35                  40                  45
Ala Leu Leu Lys Arg Thr Gly Phe His Leu Pro Val Phe Leu Tyr Ser
                50                  55                  60
Glu His Ala Val Glu Leu Pro Ala Gly Val Thr Ala Val Ile Asn Gly
65                  70                  75                  80
Asn Glu Gln Gln Trp Leu Glu Leu Glu Ser Ala Ala Cys Gln Tyr Glu
                85                  90                  95
Glu Asn Leu Leu Pro Pro Phe Tyr Asp Thr Leu Thr Gln Tyr Val Glu
                100                 105                 110
Met Gly Asn Ser Thr Phe Ala Cys Pro Gly His Gln His Gly Ala Phe
                115                 120                 125
Phe Lys Lys His Pro Ala Gly Arg His Phe Tyr Asp Phe Phe Gly Glu
                130                 135                 140
Asn Val Phe Arg Ala Asp Met Cys Asn Ala Asp Val Lys Leu Gly Asp
145                 150                 155                 160
Leu Leu Gly His Ala Gly Ser Ala Lys Asp Ala Gln Lys Phe Ala Ala
                165                 170                 175
Lys Val Phe His Ala Asp Lys Thr Tyr Phe Val Leu Asn Gly Thr Ser
                180                 185                 190
Ala Ala Asn Lys Val Val Thr Asn Ala Leu Leu Thr Arg Gly Asp Leu
```

```
                195                 200                 205
    Val Leu Phe Asp Arg Asn Asn His Lys Ser Asn His His Gly Ala Leu
    210                 215                 220

Ile Gln Ala Gly Ala Thr Pro Val Tyr Leu Glu Ala Ser Arg Asn Pro
225                 230                 235                 240

Phe Gly Phe Ile Gly Ile Asp Ala His Cys Phe Asn Glu Glu Tyr
                    245                 250                 255

Leu Arg Gln Gln Ile Arg Asp Val Ala Pro Glu Lys Ala Asp Leu Pro
                    260                 265                 270

Arg Pro Tyr Arg Leu Ala Ile Ile Gln Leu Gly Thr Tyr Asp Gly Thr
                275                 280                 285

Val Tyr Asn Ala Arg Gln Val Ile Asp Thr Val Gly His Leu Cys Asp
                290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                    325                 330                 335

Pro Gly Ile Phe Val Thr Gln Ser Val His Lys Gln Gln Ala Gly Phe
                    340                 345                 350

Ser Gln Thr Ser Gln Ile His Lys Lys Asp Asn His Ile Arg Gly Gln
                355                 360                 365

Ala Arg Phe Cys Pro His Lys Arg Leu Asn Asn Ala Phe Met Leu His
    370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                    405                 410                 415

Val Glu Ile Gly Ile Glu Ala Arg Lys Ala Ile Leu Ala Arg Cys Lys
                    420                 425                 430

Leu Phe Arg Pro Phe Ile Pro Pro Val Asp Gly Lys Leu Trp Gln
                435                 440                 445

Asp Tyr Pro Thr Ser Val Leu Ala Ser Asp Arg Arg Phe Phe Ser Phe
    450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                    485                 490                 495

Ala Glu Thr Gly Glu Tyr Ser Asp Phe Gly Val Pro Ala Thr Ile Leu
                    500                 505                 510

Ala His Tyr Leu Arg Glu Asn Gly Ile Val Pro Glu Lys Cys Asp Leu
                515                 520                 525

Asn Ser Ile Leu Phe Leu Thr Pro Ala Glu Ser His Glu Lys Leu
                530                 535                 540

Ala Gln Leu Val Ala Met Leu Ala Gln Phe Glu Gln His Ile Glu Asp
    545                 550                 555                 560

Asp Ser Pro Leu Val Glu Val Leu Pro Ser Val Tyr Asn Lys Tyr Pro
                    565                 570                 575

Val Arg Tyr Arg Asp Tyr Thr Leu Arg Gln Leu Cys Gln Glu Met His
                580                 585                 590

Asp Leu Tyr Val Ser Phe Asp Val Lys Asp Leu Gln Lys Ala Met Phe
                595                 600                 605

Arg Gln Gln Ser Phe Pro Ser Val Val Met Asn Pro Gln Asp Ala His
    610                 615                 620
```

Ser Ala Tyr Ile Arg Gly Asp Val Glu Leu Val Arg Ile Arg Asp Ala
625                 630                 635                 640

Glu Gly Arg Ile Ala Glu Gly Ala Leu Pro Tyr Pro Pro Gly Val
        645                 650                 655

Leu Cys Val Val Pro Gly Glu Val Trp Gly Gly Ala Val Gln Arg Tyr
        660                 665                 670

Phe Leu Ala Leu Glu Glu Gly Val Asn Leu Leu Pro Gly Phe Ser Pro
        675                 680                 685

Glu Leu Gln Gly Val Tyr Ser Glu Thr Asp Ala Asp Gly Val Lys Arg
        690                 695                 700

Leu Tyr Gly Tyr Val Leu Lys
705                 710

<210> SEQ ID NO 51
<211> LENGTH: 711
<212> TYPE: PRT
<213> ORGANISM: Artificial Sequence
<220> FEATURE:
<223> OTHER INFORMATION: Modified ODC protein I163G E165S

<400> SEQUENCE: 51

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
                20                  25                  30

Val Ala Ala Val Val Ile Thr Ala Ala Asp Ser Arg Ser Gly Ile Leu
            35                  40                  45

Ala Leu Leu Lys Arg Thr Gly Phe His Leu Pro Val Phe Leu Tyr Ser
    50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125

Phe Lys Lys His Pro Ala Gly Arg His Phe Tyr Asp Phe Phe Gly Glu
    130                 135                 140

Asn Val Phe Arg Ala Asp Met Cys Asn Ala Asp Val Lys Leu Gly Asp
145                 150                 155                 160

Leu Leu Gly His Ser Gly Ser Ala Lys Asp Ala Gln Lys Phe Ala Ala
                165                 170                 175

Lys Val Phe His Ala Asp Lys Thr Tyr Phe Val Leu Asn Gly Thr Ser
            180                 185                 190

Ala Ala Asn Lys Val Val Thr Asn Ala Leu Leu Thr Arg Gly Asp Leu
        195                 200                 205

Val Leu Phe Asp Arg Asn Asn His Lys Ser Asn His His Gly Ala Leu
    210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270

```
Arg Pro Tyr Arg Leu Ala Ile Ile Gln Leu Gly Thr Tyr Asp Gly Thr
        275                 280                 285

Val Tyr Asn Ala Arg Gln Val Ile Asp Thr Val Gly His Leu Cys Asp
    290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Ala Gly Phe
                340                 345                 350

Ser Gln Thr Ser Gln Ile His Lys Lys Asp Asn His Ile Arg Gly Gln
    355                 360                 365

Ala Arg Phe Cys Pro His Lys Arg Leu Asn Asn Ala Phe Met Leu His
    370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415

Val Glu Ile Gly Ile Glu Ala Arg Lys Ala Ile Leu Ala Arg Cys Lys
                420                 425                 430

Leu Phe Arg Pro Phe Ile Pro Pro Val Val Asp Gly Lys Leu Trp Gln
        435                 440                 445

Asp Tyr Pro Thr Ser Val Leu Ala Ser Asp Arg Arg Phe Phe Ser Phe
        450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                485                 490                 495

Ala Glu Thr Gly Glu Tyr Ser Asp Phe Gly Val Pro Ala Thr Ile Leu
                500                 505                 510

Ala His Tyr Leu Arg Glu Asn Gly Ile Val Pro Glu Lys Cys Asp Leu
    515                 520                 525

Asn Ser Ile Leu Phe Leu Leu Thr Pro Ala Glu Ser His Glu Lys Leu
    530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
                580                 585                 590

Asp Leu Tyr Val Ser Phe Asp Val Lys Asp Leu Gln Lys Ala Met Phe
    595                 600                 605

Arg Gln Gln Ser Phe Pro Ser Val Val Met Asn Pro Gln Asp Ala His
    610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
                660                 665                 670

Phe Leu Ala Leu Glu Glu Gly Val Asn Leu Leu Pro Gly Phe Ser Pro
                675                 680                 685
```

```
Glu Leu Gln Gly Val Tyr Ser Glu Thr Asp Ala Asp Gly Val Lys Arg
690                 695                 700

Leu Tyr Gly Tyr Val Leu Lys
705                 710

<210> SEQ ID NO 52
<211> LENGTH: 711
<212> TYPE: PRT
<213> ORGANISM: Artificial Sequence
<220> FEATURE:
<223> OTHER INFORMATION: Modified ODC protein I163G E165G

<400> SEQUENCE: 52

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
                20                  25                  30

Val Ala Ala Val Val Ile Thr Ala Ala Asp Ser Arg Ser Gly Ile Leu
            35                  40                  45

Ala Leu Leu Lys Arg Thr Gly Phe His Leu Pro Val Phe Leu Tyr Ser
        50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
                100                 105                 110

Met Gly Asn Ser Thr Phe Ala Cys Pro Gly His Gln His Gly Ala Phe
            115                 120                 125

Phe Lys Lys His Pro Ala Gly Arg His Phe Tyr Asp Phe Phe Gly Glu
        130                 135                 140

Asn Val Phe Arg Ala Asp Met Cys Asn Ala Asp Val Lys Leu Gly Asp
145                 150                 155                 160

Leu Leu Gly His Gly Gly Ser Ala Lys Asp Ala Gln Lys Phe Ala Ala
                165                 170                 175

Lys Val Phe His Ala Asp Lys Thr Tyr Phe Val Leu Asn Gly Thr Ser
            180                 185                 190

Ala Ala Asn Lys Val Val Thr Asn Ala Leu Leu Thr Arg Gly Asp Leu
        195                 200                 205

Val Leu Phe Asp Arg Asn Asn His Lys Ser Asn His His Gly Ala Leu
    210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270

Arg Pro Tyr Arg Leu Ala Ile Ile Gln Leu Gly Thr Tyr Asp Gly Thr
        275                 280                 285

Val Tyr Asn Ala Arg Gln Val Ile Asp Thr Val Gly His Leu Cys Asp
    290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335
```

```
Pro Gly Ile Phe Val Thr Gln Ser Val His Lys Gln Gln Ala Gly Phe
            340                 345                 350

Ser Gln Thr Ser Gln Ile His Lys Lys Asp Asn His Ile Arg Gly Gln
        355                 360                 365

Ala Arg Phe Cys Pro His Lys Arg Leu Asn Asn Ala Phe Met Leu His
    370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415

Val Glu Ile Gly Ile Glu Ala Arg Lys Ala Ile Leu Ala Arg Cys Lys
            420                 425                 430

Leu Phe Arg Pro Phe Ile Pro Pro Val Val Asp Gly Lys Leu Trp Gln
        435                 440                 445

Asp Tyr Pro Thr Ser Val Leu Ala Ser Asp Arg Arg Phe Phe Ser Phe
    450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                485                 490                 495

Ala Glu Thr Gly Glu Tyr Ser Asp Phe Gly Val Pro Ala Thr Ile Leu
            500                 505                 510

Ala His Tyr Leu Arg Glu Asn Gly Ile Val Pro Glu Lys Cys Asp Leu
        515                 520                 525

Asn Ser Ile Leu Phe Leu Leu Thr Pro Ala Glu Ser His Glu Lys Leu
    530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
            580                 585                 590

Asp Leu Tyr Val Ser Phe Asp Val Lys Asp Leu Gln Lys Ala Met Phe
        595                 600                 605

Arg Gln Gln Ser Phe Pro Ser Val Met Asn Pro Gln Asp Ala His
    610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
            660                 665                 670

Phe Leu Ala Leu Glu Glu Gly Val Asn Leu Leu Pro Gly Phe Ser Pro
        675                 680                 685

Glu Leu Gln Gly Val Tyr Ser Glu Thr Asp Ala Asp Gly Val Lys Arg
    690                 695                 700

Leu Tyr Gly Tyr Val Leu Lys
705                 710

<210> SEQ ID NO 53
<211> LENGTH: 711
<212> TYPE: PRT
<213> ORGANISM: Artificial Sequence
<220> FEATURE:
<223> OTHER INFORMATION: Modified ODC protein I163G E165V
```

<400> SEQUENCE: 53

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
            20                  25                  30

Val Ala Ala Val Val Ile Thr Ala Ala Asp Ser Arg Ser Gly Ile Leu
        35                  40                  45

Ala Leu Leu Lys Arg Thr Gly Phe His Leu Pro Val Phe Leu Tyr Ser
    50                  55                  60

Glu His Ala Val Glu Leu Pro Ala Gly Val Thr Ala Val Ile Asn Gly
65              70                  75                  80

Asn Glu Gln Gln Trp Leu Glu Leu Ser Ala Ala Cys Gln Tyr Glu
            85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125

Phe Lys Lys His Pro Ala Gly Arg His Phe Tyr Asp Phe Phe Gly Glu
    130                 135                 140

Asn Val Phe Arg Ala Asp Met Cys Asn Ala Asp Val Lys Leu Gly Asp
145                 150                 155                 160

Leu Leu Gly His Val Gly Ser Ala Lys Asp Ala Gln Lys Phe Ala Ala
                165                 170                 175

Lys Val Phe His Ala Asp Lys Thr Tyr Phe Val Leu Asn Gly Thr Ser
            180                 185                 190

Ala Ala Asn Lys Val Val Thr Asn Ala Leu Leu Thr Arg Gly Asp Leu
        195                 200                 205

Val Leu Phe Asp Arg Asn Asn His Lys Ser Asn His His Gly Ala Leu
    210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270

Arg Pro Tyr Arg Leu Ala Ile Ile Gln Leu Gly Thr Tyr Asp Gly Thr
        275                 280                 285

Val Tyr Asn Ala Arg Gln Val Ile Asp Thr Val Gly His Leu Cys Asp
    290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Gln Ala Gly Phe
            340                 345                 350

Ser Gln Thr Ser Gln Ile His Lys Lys Asp Asn His Ile Arg Gly Gln
        355                 360                 365

Ala Arg Phe Cys Pro His Lys Arg Leu Asn Asn Ala Phe Met Leu His
    370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys 405                 410                 415
Val Glu Ile Gly Ile Glu Ala Arg Lys Ala Ile Leu Ala Arg Cys Lys
                420                 425                 430

Leu Phe Arg Pro Phe Ile Pro Pro Val Val Asp Gly Lys Leu Trp Gln
                435                 440                 445

Asp Tyr Pro Thr Ser Val Leu Ala Ser Asp Arg Arg Phe Phe Ser Phe
    450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                485                 490                 495

Ala Glu Thr Gly Glu Tyr Ser Asp Phe Gly Val Pro Ala Thr Ile Leu
                500                 505                 510

Ala His Tyr Leu Arg Glu Asn Gly Ile Val Pro Glu Lys Cys Asp Leu
                515                 520                 525

Asn Ser Ile Leu Phe Leu Leu Thr Pro Ala Glu Ser His Glu Lys Leu
    530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
                580                 585                 590

Asp Leu Tyr Val Ser Phe Asp Val Lys Asp Leu Gln Lys Ala Met Phe
                595                 600                 605

Arg Gln Gln Ser Phe Pro Ser Val Val Met Asn Pro Gln Asp Ala His
                610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
                660                 665                 670

Phe Leu Ala Leu Glu Glu Gly Val Asn Leu Leu Pro Gly Phe Ser Pro
                675                 680                 685

Glu Leu Gln Gly Val Tyr Ser Glu Thr Asp Ala Asp Gly Val Lys Arg
                690                 695                 700

Leu Tyr Gly Tyr Val Leu Lys
705                 710

<210> SEQ ID NO 54
<211> LENGTH: 711
<212> TYPE: PRT
<213> ORGANISM: Artificial Sequence
<220> FEATURE:
<223> OTHER INFORMATION: Modified ODC protein I163V E165A

<400> SEQUENCE: 54

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
                20                  25                  30

Val Ala Ala Val Val Ile Thr Ala Ala Asp Ser Arg Ser Gly Ile Leu
                35                  40                  45

Ala Leu Leu Lys Arg Thr Gly Phe His Leu Pro Val Phe Leu Tyr Ser

```
        50                  55                  60
Glu His Ala Val Glu Leu Pro Ala Gly Val Thr Ala Val Ile Asn Gly
 65                  70                  75                  80

Asn Glu Gln Gln Trp Leu Glu Leu Glu Ser Ala Ala Cys Gln Tyr Glu
                     85                  90                  95

Glu Asn Leu Leu Pro Pro Phe Tyr Asp Thr Leu Thr Gln Tyr Val Glu
                100                 105                 110

Met Gly Asn Ser Thr Phe Ala Cys Pro Gly His Gln His Gly Ala Phe
                115                 120                 125

Phe Lys Lys His Pro Ala Gly Arg His Phe Tyr Asp Phe Phe Gly Glu
            130                 135                 140

Asn Val Phe Arg Ala Asp Met Cys Asn Ala Asp Val Lys Leu Gly Asp
145                 150                 155                 160

Leu Leu Val His Ala Gly Ser Ala Lys Asp Ala Gln Lys Phe Ala Ala
                165                 170                 175

Lys Val Phe His Ala Asp Lys Thr Tyr Phe Val Leu Asn Gly Thr Ser
                180                 185                 190

Ala Ala Asn Lys Val Val Thr Asn Ala Leu Leu Thr Arg Gly Asp Leu
            195                 200                 205

Val Leu Phe Asp Arg Asn Asn His Lys Ser Asn His His Gly Ala Leu
210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270

Arg Pro Tyr Arg Leu Ala Ile Ile Gln Leu Gly Thr Tyr Asp Gly Thr
                275                 280                 285

Val Tyr Asn Ala Arg Gln Val Ile Asp Thr Val Gly His Leu Cys Asp
290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Gln Ala Gly Phe
                340                 345                 350

Ser Gln Thr Ser Gln Ile His Lys Lys Asp Asn His Ile Arg Gly Gln
            355                 360                 365

Ala Arg Phe Cys Pro His Lys Arg Leu Asn Asn Ala Phe Met Leu His
            370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415

Val Glu Ile Gly Ile Glu Ala Arg Lys Ala Ile Leu Ala Arg Cys Lys
                420                 425                 430

Leu Phe Arg Pro Phe Ile Pro Pro Val Val Asp Gly Lys Leu Trp Gln
            435                 440                 445

Asp Tyr Pro Thr Ser Val Leu Ala Ser Asp Arg Arg Phe Phe Ser Phe
            450                 455                 460

Glu Pro Gly Ala Lys Trp His Gly Phe Glu Gly Tyr Ala Ala Asp Gln
465                 470                 475                 480
```

```
Tyr Phe Val Asp Pro Cys Lys Leu Leu Leu Thr Thr Pro Gly Ile Asp
                485                 490                 495
Ala Glu Thr Gly Glu Tyr Ser Asp Phe Gly Val Pro Ala Thr Ile Leu
            500                 505                 510
Ala His Tyr Leu Arg Glu Asn Gly Ile Val Pro Glu Lys Cys Asp Leu
        515                 520                 525
Asn Ser Ile Leu Phe Leu Thr Pro Ala Glu Ser His Glu Lys Leu
    530                 535                 540
Ala Gln Leu Val Ala Met Leu Ala Gln Phe Glu Gln His Ile Glu Asp
545                 550                 555                 560
Asp Ser Pro Leu Val Glu Val Leu Pro Ser Val Tyr Asn Lys Tyr Pro
                565                 570                 575
Val Arg Tyr Arg Asp Tyr Thr Leu Arg Gln Leu Cys Gln Glu Met His
            580                 585                 590
Asp Leu Tyr Val Ser Phe Asp Val Lys Asp Leu Gln Lys Ala Met Phe
        595                 600                 605
Arg Gln Gln Ser Phe Pro Ser Val Val Met Asn Pro Gln Asp Ala His
    610                 615                 620
Ser Ala Tyr Ile Arg Gly Asp Val Glu Leu Val Arg Ile Arg Asp Ala
625                 630                 635                 640
Glu Gly Arg Ile Ala Ala Glu Gly Ala Leu Pro Tyr Pro Pro Gly Val
                645                 650                 655
Leu Cys Val Val Pro Gly Glu Val Trp Gly Gly Ala Val Gln Arg Tyr
            660                 665                 670
Phe Leu Ala Leu Glu Glu Val Asn Leu Leu Pro Gly Phe Ser Pro
        675                 680                 685
Glu Leu Gln Gly Val Tyr Ser Glu Thr Asp Ala Asp Gly Val Lys Arg
    690                 695                 700
Leu Tyr Gly Tyr Val Leu Lys
705                 710

<210> SEQ ID NO 55
<211> LENGTH: 711
<212> TYPE: PRT
<213> ORGANISM: Artificial Sequence
<220> FEATURE:
<223> OTHER INFORMATION: Modified ODC protein I163V E165S

<400> SEQUENCE: 55

Met Lys Ser Met Asn Ile Ala Ala Ser Ser Glu Leu Val Ser Arg Leu
1               5                   10                  15
Ser Ser His Arg Arg Val Val Ala Leu Gly Asp Thr Asp Phe Thr Asp
                20                  25                  30
Val Ala Ala Val Val Ile Thr Ala Ala Asp Ser Arg Ser Gly Ile Leu
            35                  40                  45
Ala Leu Leu Lys Arg Thr Gly Phe His Leu Pro Val Phe Leu Tyr Ser
        50                  55                  60
Glu His Ala Val Glu Leu Pro Ala Gly Val Thr Ala Val Ile Asn Gly
65                  70                  75                  80
Asn Glu Gln Gln Trp Leu Glu Leu Glu Ser Ala Ala Cys Gln Tyr Glu
                85                  90                  95
Glu Asn Leu Leu Pro Pro Phe Tyr Asp Thr Leu Thr Gln Tyr Val Glu
            100                 105                 110
Met Gly Asn Ser Thr Phe Ala Cys Pro Gly His Gln His Gly Ala Phe
        115                 120                 125
```

```
Phe Lys Lys His Pro Ala Gly Arg His Phe Tyr Asp Phe Gly Glu
    130                 135                 140
Asn Val Phe Arg Ala Asp Met Cys Asn Ala Asp Val Lys Leu Gly Asp
145                 150                 155                 160
Leu Leu Val His Ser Gly Ser Ala Lys Asp Ala Gln Lys Phe Ala Ala
                165                 170                 175
Lys Val Phe His Ala Asp Lys Thr Tyr Phe Val Leu Asn Gly Thr Ser
                180                 185                 190
Ala Ala Asn Lys Val Val Thr Asn Ala Leu Leu Thr Arg Gly Asp Leu
        195                 200                 205
Val Leu Phe Asp Arg Asn Asn His Lys Ser Asn His His Gly Ala Leu
    210                 215                 220
Ile Gln Ala Gly Ala Thr Pro Val Tyr Leu Glu Ala Ser Arg Asn Pro
225                 230                 235                 240
Phe Gly Phe Ile Gly Gly Ile Asp Ala His Cys Phe Asn Glu Glu Tyr
                245                 250                 255
Leu Arg Gln Gln Ile Arg Asp Val Ala Pro Glu Lys Ala Asp Leu Pro
                260                 265                 270
Arg Pro Tyr Arg Leu Ala Ile Ile Gln Leu Gly Thr Tyr Asp Gly Thr
                275                 280                 285
Val Tyr Asn Ala Arg Gln Val Ile Asp Thr Val Gly His Leu Cys Asp
    290                 295                 300
Tyr Ile Leu Phe Asp Ser Ala Trp Val Gly Tyr Glu Gln Phe Ile Pro
305                 310                 315                 320
Met Met Ala Asp Ser Ser Pro Leu Leu Leu Glu Leu Asn Glu Asn Asp
                325                 330                 335
Pro Gly Ile Phe Val Thr Gln Ser Val His Lys Gln Gln Ala Gly Phe
                340                 345                 350
Ser Gln Thr Ser Gln Ile His Lys Lys Asp Asn His Ile Arg Gly Gln
                355                 360                 365
Ala Arg Phe Cys Pro His Lys Arg Leu Asn Asn Ala Phe Met Leu His
        370                 375                 380
Ala Ser Thr Ser Pro Phe Tyr Pro Leu Phe Ala Ala Leu Asp Val Asn
385                 390                 395                 400
Ala Lys Ile His Glu Gly Glu Ser Gly Arg Arg Leu Trp Ala Glu Cys
                405                 410                 415
Val Glu Ile Gly Ile Glu Ala Arg Lys Ala Ile Leu Ala Arg Cys Lys
                420                 425                 430
Leu Phe Arg Pro Phe Ile Pro Pro Val Val Asp Gly Lys Leu Trp Gln
        435                 440                 445
Asp Tyr Pro Thr Ser Val Leu Ala Ser Asp Arg Arg Phe Phe Ser Phe
    450                 455                 460
Glu Pro Gly Ala Lys Trp His Gly Phe Glu Gly Tyr Ala Ala Asp Gln
465                 470                 475                 480
Tyr Phe Val Asp Pro Cys Lys Leu Leu Leu Thr Thr Pro Gly Ile Asp
                485                 490                 495
Ala Glu Thr Gly Glu Tyr Ser Asp Phe Gly Val Pro Ala Thr Ile Leu
                500                 505                 510
Ala His Tyr Leu Arg Glu Asn Gly Ile Val Pro Glu Lys Cys Asp Leu
        515                 520                 525
Asn Ser Ile Leu Phe Leu Leu Thr Pro Ala Glu Ser His Glu Lys Leu
530                 535                 540
```

```
Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
            580                 585                 590

Asp Leu Tyr Val Ser Phe Asp Val Lys Asp Leu Gln Lys Ala Met Phe
        595                 600                 605

Arg Gln Gln Ser Phe Pro Ser Val Val Met Asn Pro Gln Asp Ala His
    610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
                660                 665                 670

Phe Leu Ala Leu Glu Gly Val Asn Leu Leu Pro Gly Phe Ser Pro
        675                 680                 685

Glu Leu Gln Gly Val Tyr Ser Glu Thr Asp Ala Asp Gly Val Lys Arg
690                 695                 700

Leu Tyr Gly Tyr Val Leu Lys
705                 710

<210> SEQ ID NO 56
<211> LENGTH: 711
<212> TYPE: PRT
<213> ORGANISM: Artificial Sequence
<220> FEATURE:
<223> OTHER INFORMATION: Modified ODC protein I163V E165G

<400> SEQUENCE: 56

Met Lys Ser Met Asn Ile Ala Ala Ser Glu Leu Val Ser Arg Leu
1               5                   10                  15

Ser Ser His Arg Arg Val Val Ala Leu Gly Asp Thr Asp Phe Thr Asp
                20                  25                  30

Val Ala Ala Val Val Ile Thr Ala Ala Asp Ser Arg Ser Gly Ile Leu
            35                  40                  45

Ala Leu Leu Lys Arg Thr Gly Phe His Leu Pro Val Phe Leu Tyr Ser
        50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125

Phe Lys Lys His Pro Ala Gly Arg His Phe Tyr Asp Phe Phe Gly Glu
    130                 135                 140

Asn Val Phe Arg Ala Asp Met Cys Asn Ala Asp Val Lys Leu Gly Asp
145                 150                 155                 160

Leu Leu Val His Gly Ser Ala Lys Asp Ala Gln Lys Phe Ala Ala
                165                 170                 175

Lys Val Phe His Ala Asp Lys Thr Tyr Phe Val Leu Asn Gly Thr Ser
            180                 185                 190
```

```
Ala Ala Asn Lys Val Val Thr Asn Ala Leu Leu Thr Arg Gly Asp Leu
            195                 200                 205

Val Leu Phe Asp Arg Asn Asn His Lys Ser Asn His His Gly Ala Leu
    210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270

Arg Pro Tyr Arg Leu Ala Ile Ile Gln Leu Gly Thr Tyr Asp Gly Thr
            275                 280                 285

Val Tyr Asn Ala Arg Gln Val Ile Asp Thr Val Gly His Leu Cys Asp
    290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Glu Leu Asn Glu Asn Asp
                325                 330                 335

Pro Gly Ile Phe Val Thr Gln Ser Val His Lys Gln Gln Ala Gly Phe
            340                 345                 350

Ser Gln Thr Ser Gln Ile His Lys Lys Asp Asn His Ile Arg Gly Gln
            355                 360                 365

Ala Arg Phe Cys Pro His Lys Arg Leu Asn Asn Ala Phe Met Leu His
            370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415

Val Glu Ile Gly Ile Glu Ala Arg Lys Ala Ile Leu Ala Arg Cys Lys
            420                 425                 430

Leu Phe Arg Pro Phe Ile Pro Pro Val Val Asp Gly Lys Leu Trp Gln
            435                 440                 445

Asp Tyr Pro Thr Ser Val Leu Ala Ser Asp Arg Arg Phe Phe Ser Phe
    450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                485                 490                 495

Ala Glu Thr Gly Glu Tyr Ser Asp Phe Gly Val Pro Ala Thr Ile Leu
            500                 505                 510

Ala His Tyr Leu Arg Glu Asn Gly Ile Val Pro Glu Lys Cys Asp Leu
            515                 520                 525

Asn Ser Ile Leu Phe Leu Thr Pro Ala Glu Ser His Glu Lys Leu
    530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
            565                 570                 575

Val Arg Tyr Arg Asp Tyr Thr Leu Arg Gln Leu Cys Gln Glu Met His
            580                 585                 590

Asp Leu Tyr Val Ser Phe Asp Val Lys Asp Leu Gln Lys Ala Met Phe
            595                 600                 605

Arg Gln Gln Ser Phe Pro Ser Val Val Met Asn Pro Gln Asp Ala His
```

```
                    610                 615                 620
Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                    645                 650                 655

Leu Cys Val Val Pro Gly Glu Val Trp Gly Ala Val Gln Arg Tyr
                    660                 665                 670

Phe Leu Ala Leu Glu Glu Gly Val Asn Leu Leu Pro Gly Phe Ser Pro
                675                 680                 685

Glu Leu Gln Gly Val Tyr Ser Glu Thr Asp Ala Asp Gly Val Lys Arg
            690                 695                 700

Leu Tyr Gly Tyr Val Leu Lys
705                 710

<210> SEQ ID NO 57
<211> LENGTH: 711
<212> TYPE: PRT
<213> ORGANISM: Artificial Sequence
<220> FEATURE:
<223> OTHER INFORMATION: Modified ODC protein I163V E165V

<400> SEQUENCE: 57

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
                20                  25                  30

Val Ala Val Val Ile Thr Ala Ala Asp Ser Arg Ser Gly Ile Leu
            35                  40                  45

Ala Leu Leu Lys Arg Thr Gly Phe His Leu Pro Val Phe Leu Tyr Ser
    50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125

Phe Lys Lys His Pro Ala Gly Arg His Phe Tyr Asp Phe Phe Gly Glu
    130                 135                 140

Asn Val Phe Arg Ala Asp Met Cys Asn Ala Asp Val Lys Leu Gly Asp
145                 150                 155                 160

Leu Leu Val His Val Gly Ser Ala Lys Asp Ala Gln Lys Phe Ala Ala
                165                 170                 175

Lys Val Phe His Ala Asp Lys Thr Tyr Phe Val Leu Asn Gly Thr Ser
            180                 185                 190

Ala Ala Asn Lys Val Val Thr Asn Ala Leu Leu Thr Arg Gly Asp Leu
        195                 200                 205

Val Leu Phe Asp Arg Asn Asn His Lys Ser Asn His His Gly Ala Leu
    210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
```

```
                    260                 265                 270
        Arg Pro Tyr Arg Leu Ala Ile Ile Gln Leu Gly Thr Tyr Asp Gly Thr
                        275                 280                 285
        Val Tyr Asn Ala Arg Gln Val Ile Asp Thr Val Gly His Leu Cys Asp
                        290                 295                 300
        Tyr Ile Leu Phe Asp Ser Ala Trp Val Gly Tyr Glu Gln Phe Ile Pro
        305                 310                 315                 320
        Met Met Ala Asp Ser Ser Pro Leu Leu Glu Leu Asn Glu Asn Asp
                            325                 330                 335
        Pro Gly Ile Phe Val Thr Gln Ser Val His Lys Gln Ala Gly Phe
                        340                 345                 350
        Ser Gln Thr Ser Gln Ile His Lys Lys Asp Asn His Ile Arg Gly Gln
                        355                 360                 365
        Ala Arg Phe Cys Pro His Lys Arg Leu Asn Asn Ala Phe Met Leu His
                        370                 375                 380
        Ala Ser Thr Ser Pro Phe Tyr Pro Leu Phe Ala Ala Leu Asp Val Asn
        385                 390                 395                 400
        Ala Lys Ile His Glu Gly Glu Ser Gly Arg Arg Leu Trp Ala Glu Cys
                            405                 410                 415
        Val Glu Ile Gly Ile Glu Ala Arg Lys Ala Ile Leu Ala Arg Cys Lys
                        420                 425                 430
        Leu Phe Arg Pro Phe Ile Pro Pro Val Asp Gly Lys Leu Trp Gln
                        435                 440                 445
        Asp Tyr Pro Thr Ser Val Leu Ala Ser Asp Arg Arg Phe Phe Ser Phe
                        450                 455                 460
        Glu Pro Gly Ala Lys Trp His Gly Phe Glu Gly Tyr Ala Ala Asp Gln
        465                 470                 475                 480
        Tyr Phe Val Asp Pro Cys Lys Leu Leu Leu Thr Thr Pro Gly Ile Asp
                            485                 490                 495
        Ala Glu Thr Gly Glu Tyr Ser Asp Phe Gly Val Pro Ala Thr Ile Leu
                        500                 505                 510
        Ala His Tyr Leu Arg Glu Asn Gly Ile Val Pro Glu Lys Cys Asp Leu
                        515                 520                 525
        Asn Ser Ile Leu Phe Leu Thr Pro Ala Glu Ser His Glu Lys Leu
        530                 535                 540
        Ala Gln Leu Val Ala Met Leu Ala Gln Phe Glu Gln His Ile Glu Asp
        545                 550                 555                 560
        Asp Ser Pro Leu Val Glu Val Leu Pro Ser Val Tyr Asn Lys Tyr Pro
                            565                 570                 575
        Val Arg Tyr Arg Asp Tyr Thr Leu Arg Gln Leu Cys Gln Glu Met His
                        580                 585                 590
        Asp Leu Tyr Val Ser Phe Asp Val Lys Asp Leu Gln Lys Ala Met Phe
                        595                 600                 605
        Arg Gln Gln Ser Phe Pro Ser Val Val Met Asn Pro Gln Asp Ala His
                        610                 615                 620
        Ser Ala Tyr Ile Arg Gly Asp Val Glu Leu Val Arg Ile Arg Asp Ala
        625                 630                 635                 640
        Glu Gly Arg Ile Ala Ala Glu Gly Ala Leu Pro Tyr Pro Pro Gly Val
                            645                 650                 655
        Leu Cys Val Val Pro Gly Glu Val Trp Gly Gly Ala Val Gln Arg Tyr
                        660                 665                 670
        Phe Leu Ala Leu Glu Glu Gly Val Asn Leu Leu Pro Gly Phe Ser Pro
                        675                 680                 685
```

```
Glu Leu Gln Gly Val Tyr Ser Glu Thr Asp Ala Asp Gly Val Lys Arg
        690             695                 700

Leu Tyr Gly Tyr Val Leu Lys
705             710
```